US011655444B2

(12) United States Patent
Haase et al.

(10) Patent No.: US 11,655,444 B2
(45) Date of Patent: May 23, 2023

(54) METHODS, DEVICES, AND COMPUTER PROGRAM PRODUCTS FOR STANDARDIZING A FERMENTATION PROCESS

(71) Applicant: PRECISION FERMENTATION, INC., Durham, NC (US)

(72) Inventors: Steven B. Haase, Pittsboro, NC (US); Adam R. Leman, Chapel Hill, NC (US); David S. Morris, Durham, NC (US); Ashlee M. Valente, Cary, NC (US)

(73) Assignee: PRECISION FERMENTATION, INC., Durham, NC (US)

(*) Notice: Subject to any disclaimer, the term of this patent is extended or adjusted under 35 U.S.C. 154(b) by 1057 days.

(21) Appl. No.: 16/142,736

(22) Filed: Sep. 26, 2018

(65) Prior Publication Data

US 2019/0093065 A1  Mar. 28, 2019

Related U.S. Application Data

(60) Provisional application No. 62/564,816, filed on Sep. 28, 2017.

(51) Int. Cl.
| | | |
|---|---|---|
| *C12M 1/36* | (2006.01) |
| *C12N 1/16* | (2006.01) |
| *C12N 1/20* | (2006.01) |
| *C12Q 1/06* | (2006.01) |
| *C12N 15/10* | (2006.01) |
| *C12N 1/12* | (2006.01) |
| *G16B 20/00* | (2019.01) |
| *G16B 25/00* | (2019.01) |
| *G16B 50/00* | (2019.01) |
| *C12C 11/00* | (2006.01) |
| *G16B 25/10* | (2019.01) |
| *C12Q 1/6809* | (2018.01) |
| *C12N 1/18* | (2006.01) |
| *C12Q 1/68* | (2018.01) |
| *C12Q 1/6806* | (2018.01) |
| *G16B 5/30* | (2019.01) |
| *C12R 1/225* | (2006.01) |
| *C12R 1/865* | (2006.01) |

(52) U.S. Cl.
CPC ............. *C12M 41/48* (2013.01); *C12C 11/00* (2013.01); *C12N 1/12* (2013.01); *C12N 1/16* (2013.01); *C12N 1/18* (2013.01); *C12N 1/185* (2021.05); *C12N 1/20* (2013.01); *C12N 1/205* (2021.05); *C12N 15/1003* (2013.01); *C12Q 1/06* (2013.01); *C12Q 1/68* (2013.01); *C12Q 1/6806* (2013.01); *C12Q 1/6809* (2013.01); *G16B 5/30* (2019.02); *G16B 20/00* (2019.02); *G16B 25/00* (2019.02); *G16B 25/10* (2019.02); *G16B 50/00* (2019.02); *C12R 2001/225* (2021.05); *C12R 2001/865* (2021.05)

(58) Field of Classification Search
CPC ........ C12Q 2537/165; C12Q 2545/114; C12Q 2565/607; C12Q 1/6806; C12Q 1/6809; C12Q 1/06; C12Q 1/68; C12C 11/00; C12M 41/12; C12M 41/32; C12M 41/48; C12N 15/1003; C12N 1/12; C12N 1/16; C12N 1/18; C12N 1/185; C12N 1/20; C12N 1/205; C12R 2001/225; C12R 2001/865
See application file for complete search history.

(56) References Cited

U.S. PATENT DOCUMENTS

| | | | |
|---|---|---|---|
| 4,683,207 A | 7/1987 | Waarvik | |
| 4,703,664 A | 11/1987 | Kirkpatrick et al. | |
| 6,190,914 B1* | 2/2001 | Grivell ................. | C07K 14/395 |
| | | | 435/254.11 |
| 6,874,355 B2 | 4/2005 | Kornfeldt et al. | |
| 6,874,356 B2 | 4/2005 | Kornfeldt et al. | |
| 10,498,808 B2 | 12/2019 | Purushothaman et al. | |
| 11,326,996 B2 | 5/2022 | Wells et al. | |
| 2002/0151700 A1 | 10/2002 | Farwick et al. | |
| 2004/0106170 A1 | 6/2004 | Kornfeldt et al. | |
| 2004/0112121 A1 | 6/2004 | Kornfeldt et al. | |

(Continued)

FOREIGN PATENT DOCUMENTS

| | | |
|---|---|---|
| CN | 207108972 | 3/2018 |
| WO | WO 03/029425 | 4/2003 |

(Continued)

OTHER PUBLICATIONS

S. M. G. Saerens et al. "Monitoring the influence of high-gravity brewing and fermentation temperature on flavour formation by analysis of gene expression levels in brewing yeast" Appl Microbiol Biotechnol (2008) 80:1039-1051 (Year: 2008).*

"International Search Report" and "Written Opinion of the International Searching Authority" (ISA/US) in HAASE, Steven B., et al., International Patent Application Serial No. PCT/US2018/052881, dated Dec. 6, 2018 (36 pages).

Crowell, Chris, "First look: The BrewMonitor system automates, live-streams fermentation monitoring to any device," Craft Brewing Business, Aug. 13, 2018, available at Internet webpage <https://www.craftbrewingbusiness.com/news/6000-breweries-operational-us-brewers-association-releases-2017-craft-beer-review/2018/>, accessed Sep. 6, 2018. (5 pages).

(Continued)

Primary Examiner — Blaine Lankford
(74) Attorney, Agent, or Firm — DLA Piper LLP (US)

(57) ABSTRACT

Methods of standardizing a fermentation process may include obtaining a fluidic sample, measuring one or more physical parameters of the sample, comparing the measurement of the physical parameter of the material to a baseline value of the physical parameter for the fermentation process, and responsive to a deviation of the measurement of the physical parameter from the baseline value, determining a remediation action based on a correlation between the physical parameter and regulatory genes of a fermentation organism.

6 Claims, 14 Drawing Sheets

(56) References Cited

U.S. PATENT DOCUMENTS

| | | | |
|---|---|---|---|
| 2008/0090047 A1* | 4/2008 | Kuroda | D03D 27/00 428/97 |
| 2012/0077232 A1 | 3/2012 | Budaraju et al. | |
| 2012/0295338 A1 | 11/2012 | Reep et al. | |
| 2015/0291982 A1 | 10/2015 | Budaraju et al. | |
| 2018/0322597 A1 | 11/2018 | Sher | |
| 2019/0093065 A1 | 3/2019 | Haase et al. | |
| 2020/0027079 A1 | 1/2020 | Kurian | |
| 2020/0292434 A1 | 9/2020 | Wells et al. | |
| 2020/0292501 A1 | 9/2020 | Wells et al. | |
| 2020/0294234 A1 | 9/2020 | Rance et al. | |
| 2020/0319005 A1 | 10/2020 | Folgero et al. | |

FOREIGN PATENT DOCUMENTS

| | | |
|---|---|---|
| WO | WO 2004/027092 | 4/2004 |
| WO | 2017096385 A1 | 6/2017 |
| WO | 2019067558 A1 | 4/2019 |
| WO | WO 2019/071385 | 4/2019 |

OTHER PUBLICATIONS

McGoff, K.A., Guo, X., Deckard, A., Kelliiher, C.M., Leman, A.R., Francey, L.J., Hogenesch, J.B., Haase, S.B, and Harer, J., "The Local Edge Machine: inference of dynamic models of gene regulation," Genome Biology 17:214, published Oct. 19, 2016 (13 pages).

English Abstract of CN 207108972 published on Mar. 16, 2018.

Written Opinion issued in Application No. PCT/US22/33269 dated Oct. 17, 2022.

International Search Report issued in Application No. PCT/US22/33269 dated Oct. 17, 2022.

Yokogawa Electric Corportion, "Automatic and Continuous Monitoring of the Beer Fermentation Process (with a Liquid Density Meter)", YOKOGAWA Homepage, 2020, 1-3 page, URL: https://www.yokogawa.com.eu/library/resources/application-notes/automatic-and-continuous-monitoring-of-the-beer-fermentation-process-with-a-liquid-density-meter.

Written Opinion issued in Application No. PCT/US22/070793 dated Jun. 9, 2022.

International Search Report issued in Application No. PCT/US22/070793 dated Jun. 9, 2022.

Michael D.G. et al., "Model-based transcriptome engineering promotes a fermentative transcritiopnal state in yeast", Proceedings of the National Academy of Sciences, vol. 113, No. 47, pps. (Nov. 3, 2016).

Written Opinion issued in European Application No. 18863516.3 dated May 26, 2021.

International Search Report issued European Application No. PCT/US22/070793 dated May 26, 2021.

Image File Wrapper of U.S. Appl. No. 17/652,402 electronically captured from PAIR on Dec. 22, 2022.

Image File Wrapper of U.S. Appl. No. 17/652,402 electronically capture from PAIR from Feb. 1, 2023 to Apr. 6, 2023.

\* cited by examiner

METHODS, DEVICES, AND COMPUTER PROGRAM PRODUCTS FOR STANDARDIZING A FERMENTATION PROCESS

CROSS-REFERENCE TO RELATED APPLICATIONS

The present application is a U.S. nonprovisional patent application of, and claims priority under 35 U.S.C. § 119(e) to, U.S. provisional patent application Ser. No. 62/564,816, filed Sep. 28, 2017, and entitled, "METHODS, DEVICES, AND COMPUTER PROGRAM PRODUCTS FOR YEAST PERFORMANCE MONITORING IN FERMENTATION SYSTEMS," which provisional patent application is incorporated by reference herein in its entirety.

FIELD

Various embodiments described herein relate to methods, devices, and computer program products for fermentations systems and, more particularly, to fermentations systems that incorporate yeast monitoring.

BACKGROUND

Fermentation of grain extracts for the purpose of ethanol production by *Saccharomyces cerevisiae* and other microorganisms is an ancient invention. In spite of much progress, control of this process is still very primitive. Modern fermentation facilities are equipped to: receive feedstocks of grain, fruit, and other organic material; extract soluble fermentable sugars using heat, enzymes, and mechanical action; perhaps adding preservative or flavoring plants such as hops; and move this fermentable substrate to fermenters where yeast is added. Various yeast species (and subspecies, or strains) are able to convert much of the present sugars to carbon dioxide and ethanol, yielding ethanol-containing beverages, especially beer. Successful fermentations end when the beer reaches the desired alcohol content and has other flavor and color characteristics consistent with a particular beer style. However, once a fermentation is initiated by mixing yeast and wort in a fermentation vessel, the brewer has almost as little control over the process as his ancient predecessors who may have simply exclaimed, *Alea iacta* est. Other fermentation processes, such as those used to produce other food and beverage products or fine chemicals or pharmaceuticals operate in the same way. They are begun and end when the yield targets are satisfied.

One assumption of fermentation in this way is that providing highly similar initial ingredients and conditions will yield a highly similar product. While most professional brewers succeed in routinely producing products that meet high quality thresholds, the costs of doing so are unnecessarily high because the time required for the fermentations and certain output characteristics often vary in ways that cannot be anticipated at the outset and may not be known for several days or even prior to the end of the fermentation.

SUMMARY

Various embodiments described herein provide methods, devices, and computer program products for the monitoring and remediation of yeast performance in fermentations systems.

According to some embodiments described herein, a fermentation monitoring system for a fermentation process using a fermentation organism includes a fluidic sampling apparatus configured to be coupled to a fermentation tank and sample material from the fermentation tank, a physical sensor array coupled to the fluidic sampling apparatus configured to provide measurements of at least one physical parameter of the material sampled from the fermentation tank, an analytic system comprising at least one processor communicatively coupled to the physical sensor array and configured to receive the measurements of the physical sensor array, and a memory coupled to the at least one processor and including computer readable program code. When executed by the at least one processor, the computer readable program code causes the at least one processor to perform operations including receiving the measurement of the at least one physical parameter of the material sampled from the fermentation tank, comparing the measurement of the at least one physical parameter of the material sampled from the fermentation tank to a baseline value of the at least one physical parameter for the fermentation process, and, responsive to a deviation of the measurement of the at least one physical parameter of the material sampled from the fermentation tank from the baseline value, determining a remediation action based on a correlation between the at least one physical parameter and one or more regulatory genes of the fermentation organism.

According to some embodiments described herein, a method for monitoring a fermentation process includes collecting a sample of material comprising a fermentation organism that is in a fermentation tank performing the fermentation process, said collecting performed by utilizing a fluidic sampling apparatus coupled to the fermentation tank, utilizing a physical sensor array coupled to the fluidic sampling apparatus to measure at least one physical parameter of the sample, comparing the measurement of the at least one physical parameter of the sample to a baseline value of the at least one physical parameter for the fermentation process, responsive to a deviation of the measurement of the at least one physical parameter of the sample from the baseline value, determining a remediation action based on a correlation between the at least one physical parameter of the sample and one or more regulatory genes of the fermentation organism, and performing the remediation action to alter a state of the material in the fermentation tank.

According to some embodiments described herein, a fermentation monitoring system for a fermentation process using a fermentation organism includes a fluidic sampling apparatus configured to be coupled to a fermentation tank and sample material from the fermentation tank, a physical sensor array coupled to the fluidic sampling apparatus configured to provide measurements of at least one physical parameter of the material sampled from the fermentation tank, an analytic system comprising at least one processor communicatively coupled to the physical sensor array and configured to receive the measurements of the physical sensor array, a storage medium coupled to the analytic system, and a memory coupled to the at least one processor and including computer readable program code. The computer readable program code, when executed by the at least one processor, causes the at least one processor to perform operations including receiving a plurality of measurements of the at least one physical parameter of the material sampled from the fermentation tank at multiple time points during the fermentation process from initiation to termination of the fermentation process, thereby providing values (or a rate of change) for the at least one physical parameter over time for the fermentation process, measuring a transcriptome of the fermentation organism at the time points during the fermentation process as measured for the at least one physical parameter to produce a gene expression database over time for the fermentation process, inferring regulatory networks of the fermentation organism from the gene expression database, identifying one or more regulatory genes of the fermentation organism that are correlated with a value or range of values (or a rate of change) for the at least one physical parameter measured for the fermentation process, thereby constructing a baseline database for the fermentation process that provides a predetermined value or range of values (or predetermined rate of change) for the at least one physical parameter that is correlated with the one or more regulatory genes of the fermentation organism, and storing the baseline database in the storage medium.

According to some embodiments described herein, a method for constructing a baseline database for a selected fermentation process by a fermentation organism in a fermentation substrate, includes (a) measuring a physical parameter at multiple time points during the selected fermentation process from initiation to termination of the selected fermentation process, thereby providing values (or a rate of change) for the physical parameter over time for the selected fermentation process, (b) measuring a transcriptome of the fermentation organism at the same time points during the fermentation process as measured for the physical parameter to produce a gene expression database over time for the selected fermentation process, (c) inferring regulatory networks of the fermentation organism from the gene expression database, and (d) identifying one or more regulatory genes of the fermentation organism that are correlated with a value or range of values (or a rate of change) for the physical parameter measured for the selected fermentation process, thereby constructing the baseline database for the selected fermentation process that provides a predetermined value or range of values (or predetermined rate of change) for the parameter that is correlated with the one or more regulatory genes of the fermentation organism.

According to some embodiments described herein, a method of standardizing a selected fermentation process by a fermentation organism in a fermentation substrate, includes (a) measuring a physical parameter at multiple time points during the selected fermentation process from initiation to termination of the selected fermentation process, thereby providing values (or a rate of change) for the physical parameter over time for the selected fermentation process, (b) comparing values (or a rate of change) of the physical parameter measured for the selected fermentation with predetermined values (or predetermined rate of change) for the same physical parameter provided by a baseline database, (c) modifying a fermentation condition to increase or decrease the expression of one or more regulatory genes of the fermentation organism identified in the baseline database as correlated with the physical parameter when the values (or the rate of change) of the physical parameter measured for the selected fermentation process fall outside the predetermined range of values (or the predetermined rate of change) for the same physical parameter, thereby modifying/adjusting the values (or the rate of change) for the physical parameter so that they fall within the predetermined range of values (or the predetermined rate of change) of the baseline database and standardizing the selected fermentation process.

In accordance with one or more preferred embodiments described herein, a method provides a technical solution to the technical problem of standardizing a selected fermentation process by a fermentation organism in a fermentation substrate. The method includes first, constructing a baseline database for the selected fermentation process by the fermentation organism in the fermentation substrate by initiating a first instance of the selected fermentation process by the fermentation organism in the fermentation substrate and obtaining, at each respective time point of a plurality of predefined time points defined from the beginning of the initiated first instance of the fermentation process, a respective fluidic sample, measuring, using each respective fluidic sample for the first instance, one or more physical parameters for the respective fluidic sample at the corresponding respective time point, determining one or more physical parameter values for the first instance based on the measuring for the first instance, the one or more physical parameter values including values at a point in time and values representing a rate of change, and measuring, using each respective fluidic sample for the first instance, a transcriptome of the fermentation organism at the corresponding respective time point. Such measuring includes isolating RNA from the fermentation substrate of the respective fluidic sample, purifying the RNA isolated from the fermentation substrate of the respective fluidic sample, and measuring the RNA. The constructing of a baseline database further includes determining gene expression data for the selected fermentation process based on the obtained measurements by filtering determined physical parameter and gene expression data to generate a first dataset which only includes dynamic physical parameter values and dynamic gene expression values, computationally normalizing dynamic physical parameter values and dynamic gene expression values of the first dataset to generate a normalized dataset, determining one or more possible regulators by identifying dynamic gene expression values of the normalized dataset that correspond to transcription factors, and comparing normalized dynamic physical parameter values and normalized dynamic gene expression values of the normalized dataset as targets to each determined possible regulator. This is accomplished via a methodology which includes generating a regulation function for each possible regulator-target relationship, each regulation function defining a relationship between one of the determined possible regulators and a downstream gene target corresponding to one of the normalized dynamic gene expression values or a chemical change target corresponding to one of the normalized dynamic physical parameter values, calculating, for each regulator-target relationship, a score representing a fit of the corresponding possible regulator to the corresponding target, ranking each regulation-target relationship based on the calculated scores, and assigning a confidence value to each regulator-target relationship, determining a confidence threshold based at least in part on data density, and constructing a regulatory network based on the ranked regulator-target relationships and the confidence threshold. The constructing of a baseline database further includes constructing, based on the ranked regulator-target relationships and the constructed regulatory network, the baseline database for the selected fermentation process that specifies one or more condition sets each comprising a preferred value or range of values, at one or more respective time points of the plurality of predefined time points, for one or more physical parameters that have been determined based on the ranked regulator-target relationships and the constructed regulatory network to correspond to one or more regulatory genes of the fermentation organism, for each physical parameter forming part of a condition set, for each of the one or more respective time points of the plurality of predefined time points, an indication of one or more regulatory genes determined based on the ranked regulator-target relationships and the constructed regulatory network to have a relationship to that physical parameter, and for each regulatory gene indicated to have a relationship with at least one physical parameter forming part of a condition set, for each of the one or more respective time points of the plurality of predefined time points, an indication of one or more remediation actions to increase or decrease the expression of that regulatory gene. The method further includes effecting, in a fermentation vessel, a standardized instance of the selected fermentation process by the fermentation organism in the fermentation substrate by initiating a second instance of the selected fermentation process by the fermentation organism in the fermentation substrate, and automatically, at each respective time point of the plurality of predefined time points defined from the beginning of the initiated first instance of the fermentation process, obtaining a respective fluidic sample, measuring, using the respective fluidic sample for the second instance, one or more physical parameters for the respective fluidic sample at the corresponding respective time point, determining one or more physical parameter values for the second instance based on the measuring for the second instance, the one or more physical parameter values including values at a point in time and values representing a rate of change, and comparing determined physical parameter values for the second instance to preferred values and ranges of values specified in condition sets of the baseline database. Effecting the standardized instance further includes automatically identifying, as a result of comparing at a certain one of the time points determined physical parameter values for the second instance to preferred values and ranges of values specified in condition sets of the baseline database, a first physical parameter value for a first physical parameter which falls outside of a preferred range of values specified for the first physical parameter by a first condition set of the baseline database, automatically determining, via lookup in the baseline database, a first regulatory gene determined based on the ranked regulator-target relationships and the constructed regulatory network to have a relationship to the first physical parameter, automatically determining, via lookup in the baseline database, a first remediation action which will affect the expression of the determined first regulatory gene, the first remediation action comprising modifying a specified first fermentation condition, and effecting modification of the specified first fermentation condition to affect the expression of the determined first regulatory gene.

In accordance with one or more preferred embodiments with respect to the just discussed method, effecting modification may comprise automatically effecting modification.

In accordance with one or more preferred embodiments with respect to the just discussed method, this method additionally comprises, prior to effecting modification of the specified first fermentation condition to affect the expression of the determined first regulatory gene, displaying, to a user via an electronic display associated with the fermentation vessel, an indication of the first physical parameter, an indication of the first physical parameter value for the first physical parameter, an indication of the preferred range of values for the first physical parameter from the first condition set, an indication of the first regulatory gene determined based on the ranked regulator-target relationships and the constructed regulatory network to have a relationship to that physical parameter, and an indication of the first remediation action which will affect the expression of the determined first regulatory gene, the indication including an indication to modify the specified first fermentation condition.

In accordance with one or more preferred embodiments with respect to the just discussed method, this method comprises, rather than effecting modification of the specified first fermentation condition to affect the expression of the determined first regulatory gene, displaying, to a user via an electronic display associated with the fermentation vessel, an indication of the first physical parameter, an indication of the first physical parameter value for the first physical parameter, an indication of the preferred range of values for the first physical parameter from the first condition set, an indication of the first regulatory gene determined based on the ranked regulator-target relationships and the constructed regulatory network to have a relationship to that physical parameter, and an indication of the first remediation action which will affect the expression of the determined first regulatory gene, the indication including an indication to modify the specified first fermentation condition.

In accordance with one or more preferred embodiments with respect to the just discussed method, this method comprises, rather than constructing the specified baseline database, constructing a baseline database that specifies one or more condition sets each comprising a preferred value or range of values, at one or more respective time points of the plurality of predefined time points, for one or more physical parameters that have been determined based on the ranked regulator-target relationships and the constructed regulatory network to correspond to one or more regulatory genes of the fermentation organism, and, for each condition set, one or more remediation actions determined, based on the ranked regulator-target relationships and the constructed regulatory network, to increase or decrease the expression of one or more regulatory genes of the fermentation organism determined based on the ranked regulator-target relationships and the constructed regulatory network to correspond to the respective physical parameter.

In accordance with one or more preferred embodiments described herein, a method provides a technical solution to the technical problem of standardizing a selected fermentation process by a fermentation organism in a fermentation substrate. The method includes maintaining a baseline database for the selected fermentation process by the fermentation organism in the fermentation substrate including data based on ranked regulator-target relationships and a constructed regulatory network for the fermentation organism. The baseline database specifies one or more condition sets each comprising a preferred value or range of values, at one or more respective time points of a plurality of predefined time points, for one or more physical parameters that have been determined based on the ranked regulator-target relationships and the constructed regulatory network to correspond to one or more regulatory genes of the fermentation organism. The baseline database further specifies, for each physical parameter forming part of a condition set, for each of the one or more respective time points of the plurality of predefined time points, an indication of one or more regulatory genes determined based on the ranked regulator-target relationships and the constructed regulatory network to have a relationship to that physical parameter. The baseline database further specifies, for each regulatory gene indicated to have a relationship with at least one physical parameter forming part of a condition set, for each of the one or more respective time points of the plurality of predefined time points, an indication of one or more remediation actions to increase or decrease the expression of that regulatory gene.

It is noted that aspects of the inventive concepts described with respect to one embodiment, may be incorporated in a different embodiment although not specifically described relative thereto. That is, all embodiments and/or features of any embodiment can be combined in any way and/or combination. Other operations according to any of the embodiments described herein may also be performed. These and other aspects of the inventive concepts are described in detail in the specification set forth below.

BRIEF DESCRIPTION OF THE DRAWINGS

The above and other objects and features will become apparent from the following description with reference to the following figures, wherein like reference numerals refer to like parts throughout the various figures unless otherwise specified.

DETAILED DESCRIPTION

Figure 1:
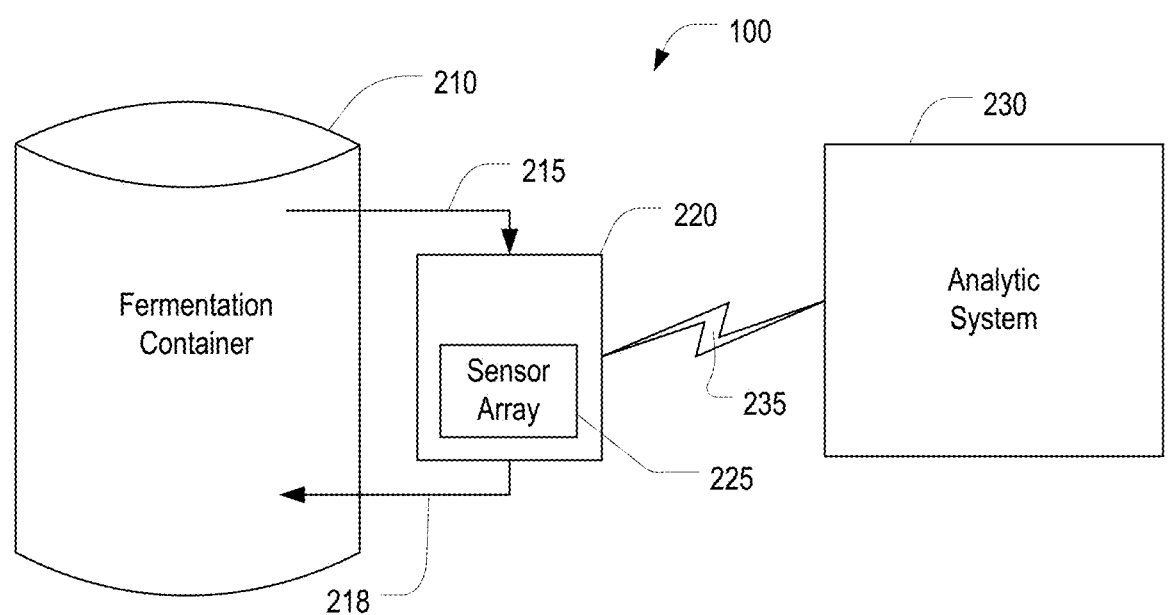
FIG. 1 illustrates a schematic representation of a monitoring system configured to monitor performance of a fermentation process, according to various embodiments as described herein. The device is composed of four parts.

Various embodiments will be described more fully hereinafter with reference to the accompanying drawings. Other embodiments may take many different forms and should not be construed as limited to the embodiments set forth herein. Like numbers refer to like elements throughout.

Methods, devices, and computer program products, as described herein, provide improved instrumentation for the monitoring of fermentations processes to track conformance to a baseline, and are able to improve deviations from the baseline through remediation based on techniques that match specific parameters of a fermentation product to regulatory genes of the underlying fermentation organism.

As previously noted, modern brewing processes utilizing, for example, yeast, can suffer from instances of variability, where the same or similar inputs yield differing results. In many cases, this variability is due to the differences in viability and vitality of the yeast population tasked with fermentation of wort/feedstock. This variability is not visible or readily measurable but has a direct and often immediate effect on the speed and activity of the fermentation. Therefore, there is a need to use real time monitoring of yeast health and performance parameters to establish baselines and guidelines for various types and kinds of fermentations, to determine whether a given fermentation process is proceeding according to pre-established norms and baselines, and to guide interventions to improve the timing of a fermentation or characteristics of the final product.

The variable nature of fermentation processes is especially apparent for beer breweries, as the product is not distilled or highly modified after primary fermentation. Therefore, beer production is used as an example for this description. However, it will be understood that the techniques and devices described herein may be equally applied to other fermentation methods without deviating from the various embodiments described herein.

As used herein, "fermentation" refers to a chemical transformation of a substance by a microorganism. Microorganisms for fermentation may include, but are not limited to, fungi (e.g., yeast), bacteria, and/or algae (e.g., microalgae).

Once a brewery develops a recipe for a particular beer, the amounts of the major ingredients such as grain (which may be malted barley, wheat, corn, rice, etc.), hops, yeast, and/or water are made standard. In addition, certain other ingredients may be added for the benefit of yeast health and metabolism and to aid in fermentation. Examples of these additives are vitamins, refined carbohydrates, minerals, pH buffers, and dissolved gases. Complicating matters further is the practice of re-pitching yeast, which amounts to reusing yeast from a completed fermentation to initiate the next fermentation.

Yeast tasked with fermentation may be placed in stressful environmental conditions and their biology and health may change each time they are re-pitched. Therefore, the nutritional and additive requirements of the yeast can change over the course of several re-pitchings. This variability is difficult for brewers to gauge without the use of sophisticated laboratory equipment and assays. As a result, levels of these additives are often set in ways that do not reflect the changing health or nutritional needs of the yeast population after a certain number of re-pitchings. The wide range of yeast strains and beer recipes in use, as well as the constant development of new strains and beer recipes further complicate all of this.

This problem is generalizable to production fermentation of distillable ethanol and other biologics. A variety of fermentable feedstocks, yeast strains, and conditions are used even if the desired fermentation product (such as fuel ethanol, biochemicals, and/or other fine chemicals) is the same. For example, though yeast is discussed, the same or similar problems occur with other fermentation organisms such as, for example, fungi (e.g., yeast), bacteria, and/or algae (e.g., microalgae).

It is difficult, if not impossible, to assign a specific nutritional requirement profile that would be useful to all breweries or fermentation facilities for all types of fermentation processes. Instead, a better tool for breweries and fermentation facilities would be the ability to monitor the yeast performance over all stages of a fermentation to determine their own route of intervention depending on the age of the yeast population (pitch number) and real measurements of chemical and/or other biologically-relevant values as they occur over time during fermentation due to the activity of the yeast. The measurements can be recorded and uploaded to a user-accessible database for analysis and record keeping. In such a system, the monitoring may be continuous, such that it does not interfere with the fermentation process. The monitoring may also be coupled to analytical tools, which permit inference of the state and activity of the yeast from the data collected in near real time so that the brewer can act upon it.

FIG. 1 illustrates schematic representation of a monitoring system 100 configured to monitor performance of a fermentation process, according to various embodiments as described herein. The monitoring system 100 may contain a mechanical and fluid apparatus 220, also described herein as a fluidic sampling apparatus 220, coupled to a fermentation container 210. The fluidic sampling apparatus 220 may be further coupled to sensor array 225, and may be communicatively coupled to analytic system 230.

The fermentation container 210 may be a container configured to contain a fermentation process. In some embodiments, the fermentation container 210 may be a fermentation tank for brewing beer. Fermentation tanks 210 may vary in size from a few gallons to thousands of gallons. Though fermentation tanks 210 are used as an example herein, it will be understood that any container capable of containing a fermentation process may be used without deviating from the various embodiments described herein.

The fluidic sampling apparatus 220 may be configured to be installed on the fermentation container 210 and to take material out of the fermentation container 210 and return it continuously. As used herein, "continuously" means that material may be taken out of the fermentation container 210 and returned to the fermentation container 210 at least once every five minutes during the fermentation process. The material may be brought in by inlet connection 215. After being sampled within the fluidic sampling apparatus 220, the material may be returned to the fermentation container 210 via outlet connection 218. In some embodiments, the material may not be returned to the fermentation container 210 (e.g., may be discarded to a drain or waste vessel).

In some embodiments, the inlet connection 215 may include multiple physical connections between the fluidic sampling apparatus 220 and the fermentation container 210. Similarly, in some embodiments, the outlet connection 218 may include multiple physical connections between the fluidic sampling apparatus 220 and the fermentation container 210. In some embodiments, the inlet connection 215 and the outlet connection 218 may be the same physical connection to the fermentation container 210.

Figure 2:
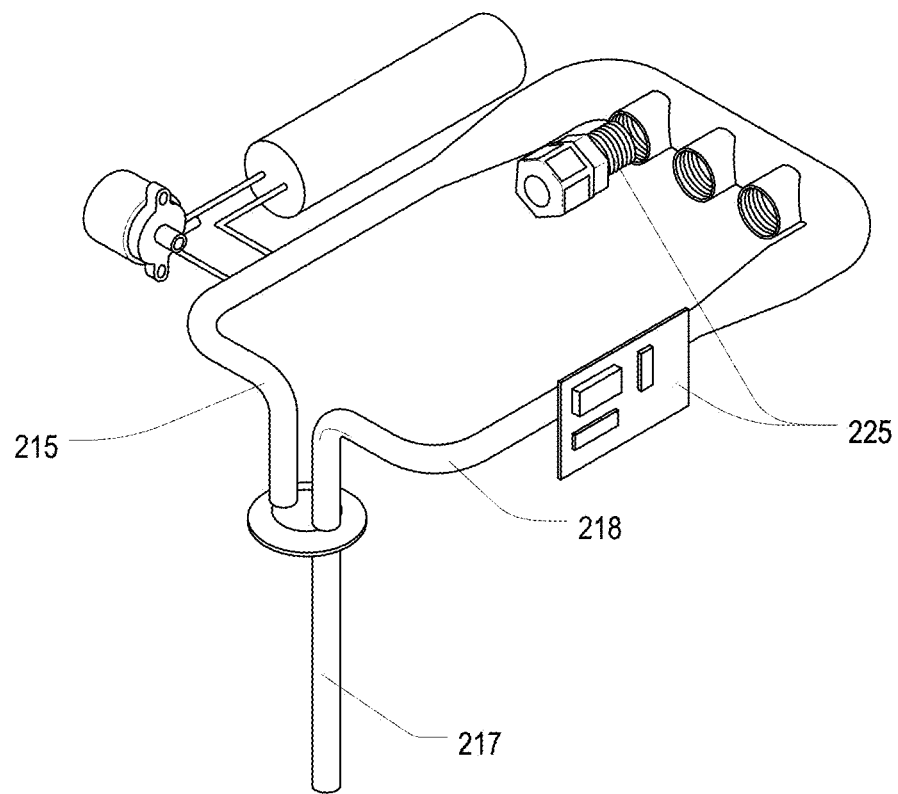
FIG. 2 illustrates a schematic representation of an example of the fluidic sampling apparatus configured to be coupled to a fermentation container, according to various embodiments as described herein.

The fluidic sampling apparatus 220 portion of the monitoring system 100 will vary with the size and type of the fermentation container 210, the pressure, flow rate, and other special requirements of the facility in which the fermentation container 210 is located. For example, in breweries there may be a requirement for the fluidic sampling apparatus 220 to be cleanable in place ('CIP') using standard, food grade chemicals and procedures. FIG. 2 illustrates a schematic representation of an example of the fluidic sampling apparatus 220 configured to be coupled to a fermentation container 210, according to various embodiments as described herein. The inlet 215 and outlet 218 tubes may both be fed through the same clamped fitting 217 so that material can be pumped out of the fermentation vessel 210, passed over a physical sensor array 225 in a sequential path and then returned to the fermentation vessel 210.

As illustrated in FIGS. 1 and 2, the fluidic sampling apparatus 220 may also be further coupled to physical sensor array 225. The physical sensor array 225 may contain one or more sensors that are configured to sample and detect physical parameters, such as chemical, biological and/or other parameters in the liquid from the fermentation container 210 that the sensors of the physical sensor array 225 are in contact with. The sensors included in the physical sensor array 225 may include any sensor capable of detecting physical parameters, including chemical, biological, and/or other parameters in the fermentation product, or the environment surrounding the fermentation product, associated with the fermentation container 210. The physical sensor array 225 may also vary with the type of product or process. For example, particular brewing processes may require additional monitoring that may require additional sensors be placed in the physical sensor array 225. The physical sensor array 225 may be capable of sampling the physical parameters at least once every 15 seconds. In some embodiments, the physical sensor array 225 may be capable of sampling the physical parameters more frequently or less frequently than 15 seconds. For example, in some embodiments, the physical sensor array 225 may be capable of sampling the physical parameters at least once every five minutes.

Figure 3:
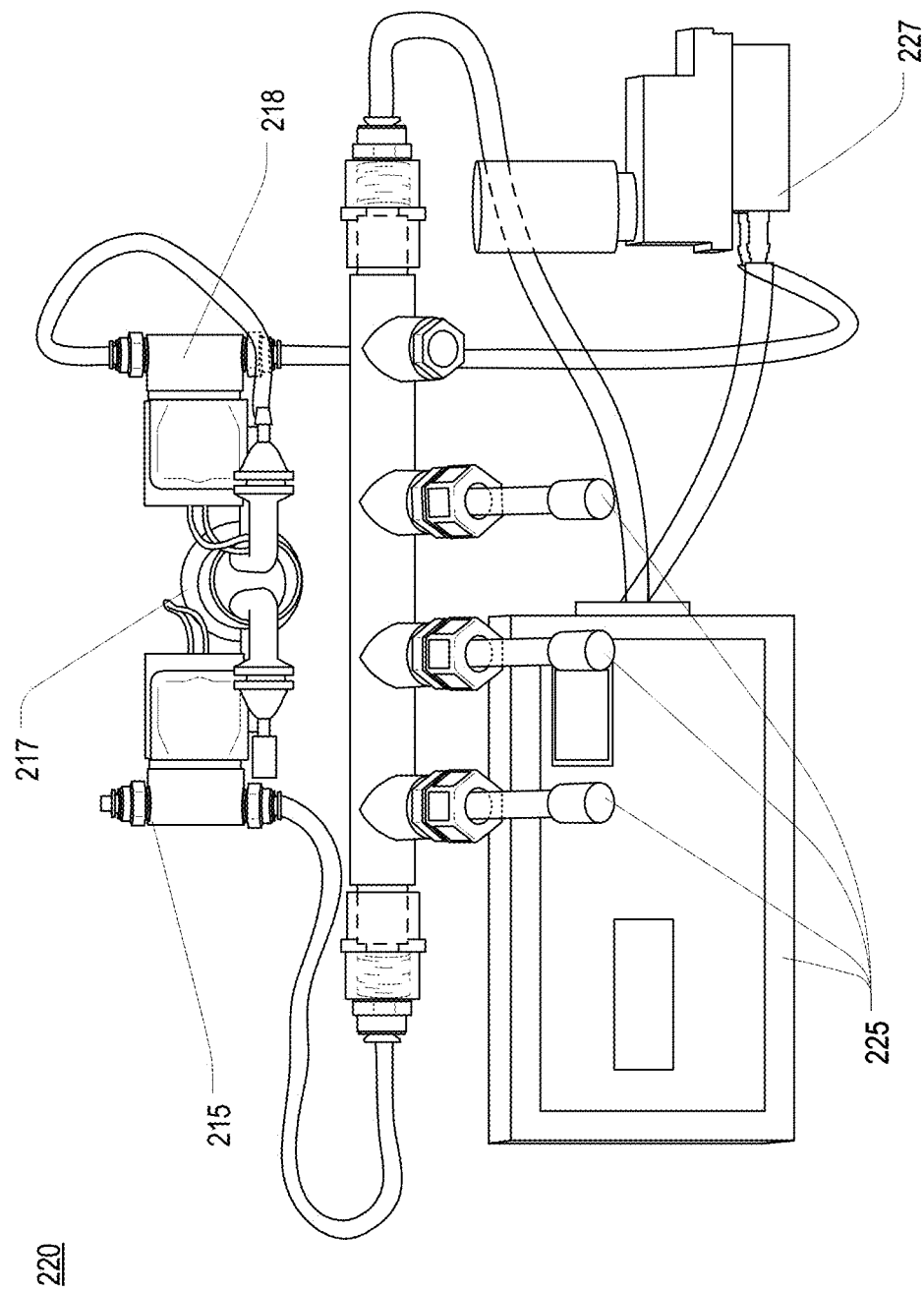
FIG. 3 illustrates a schematic representation of an example of the physical sensor array incorporated into the fluidic sampling apparatus, according to various embodiments as described herein.

FIG. 3 illustrates a schematic representation of an example of the physical sensor array 225 incorporated into the fluidic sampling apparatus 220, according to various embodiments as described herein. Referring to FIG. 3, the inlet 215 and outlet 218 tubes are fed through a clamped fitting 217 on the fermentation vessel 210. The fermentation substrate is passed through the fluidic sampling apparatus 220 by the action of a pump mechanism 227 within the fluidic sampling apparatus 220. The fermentation substrate is passed over the sensors of the physical sensor array 225 sequentially, and then returned to the fermentation vessel 210. The physical sensor array 225 may include sensors measuring physical parameters such as chemical, biological and/or other parameters in the liquid fermentation substrate and may contain additional sensors measuring physical parameters of the gases emitted by the fermentation process. The sensors of the physical sensor array 225 may be configured to monitor the ability of yeast to change the environment of the fermentation container 210 and analyze these environmental changes for the purposes of measuring and assessing the internal state and fermentation performance of the yeast population in the fermentation container 210. The liquid sensors are placed in a mechanical/fluidics unit that is fitted onto a standard port (e.g., inlet connection 215) of the fermentation container 210. The physical sensor array 225 may be attached only to one port and may be sufficiently lightweight to require no other support. Though yeast is used as an example fermentation organism, it will be understood that physical parameters of the fermentation process associated with other fermentation organisms is possible without deviating from the embodiments described herein. For example, other fermentation organisms that may be monitored include bacteria, algae, and/or other fungi, though the embodiments described herein are not limited thereto.

The fluidic sampling apparatus 220 may have a fluidics system that samples liquid across or through the physical sensor array 225 using a pump. The liquid may then be returned to the fermentation container 210 through the outlet connection 218 through a length of tubing to return the liquid to a different physical location within the fermentation container 210. In some embodiments, the pump of the fluidic sampling apparatus 220 may be continuously operated during a fermentation.

Figure 4:
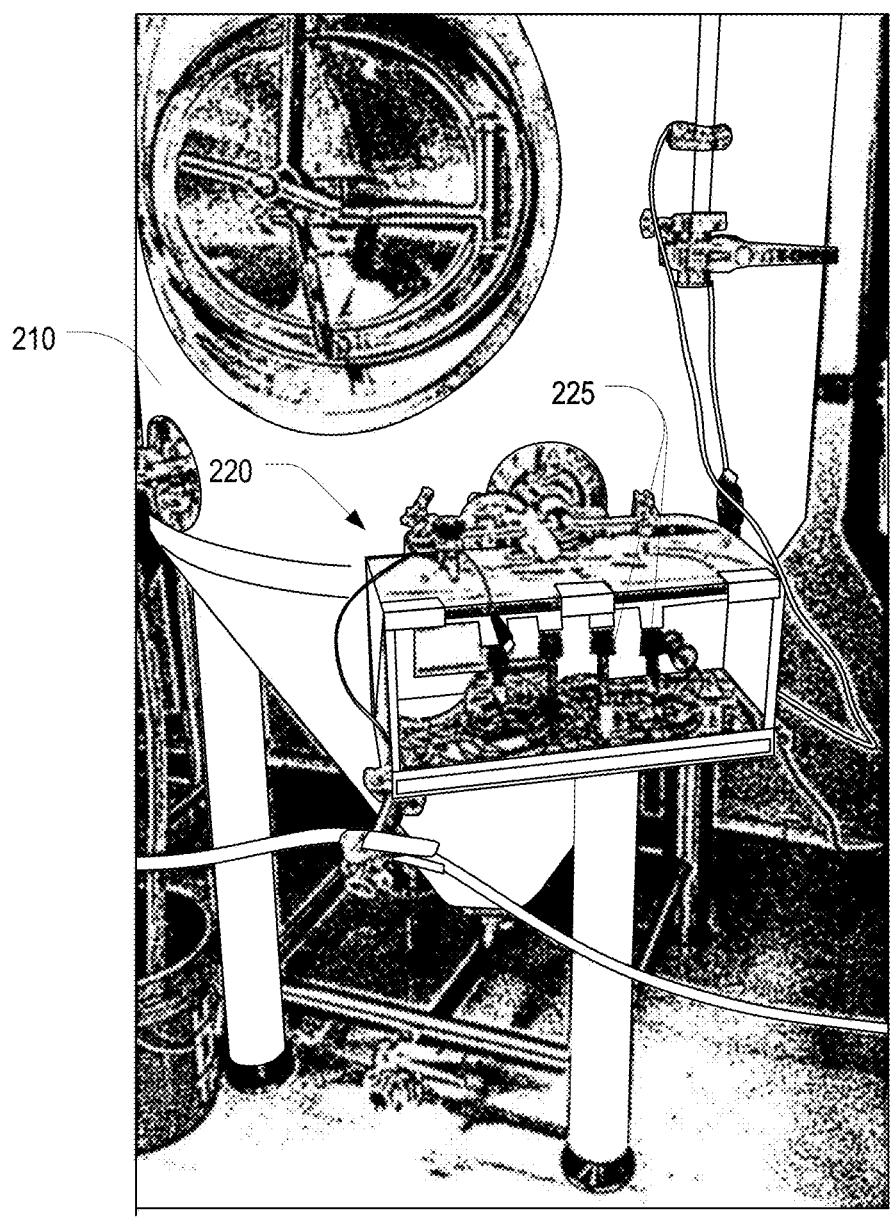
FIG. 4 illustrates the physical sensor array and the fluidic sampling apparatus coupled to a fermentation container, according to various embodiments described herein.

The physical sensor array 225 may measure physical parameters of the liquid inside the fermentation container 210, including but not limited to chemical properties, temperature, pH, dissolved oxygen content, ethanol level, $CO_2$ level, liquid density, gravity, cell concentration, and/or electrical conductivity, though the embodiments described herein are not limited thereto. A portion of the physical sensor array 225 may be placed on an off-gassing arm of the fermentation container 210 and may measure gas flow volume and the levels of specific gases, including but not limited to carbon dioxide contained in the off-gas produced by the fermentation process. The various portions of the physical sensor array 225 may be connected by either a wireless or wired connection depending on model. In some embodiments, the sensors of the physical sensor array 225 may be connected by a common circuit board that allows for coordination of sampling, time stamping of each data point, data storage, and upload of sensor data by wireless transmission to off-site servers. FIG. 4 illustrates the physical sensor array 225 and the fluidic sampling apparatus 220 coupled to a fermentation container 210, according to various embodiments described herein.

The monitoring system 100 may also include an analytic system 230. The analytic system 230 may be communicatively coupled to the physical sensor array 225 and the fluidic sampling apparatus 220 to control the sensors of the physical sensor array 225, read the output of the physical sensor array 225, and analyze the output to determine if remediation is necessary for the fermentation process occurring in the fermentation container 210.

The analytic system 230 may be communicatively coupled to the fluidic sampling apparatus 220 via communication path 235. The communication path 235 may be implemented via various different technologies to communicate between the analytic system 230 and the fluidic sampling apparatus 220. For example, the communication path 235 may be implemented using Radio Frequency Identification (RFID), Bluetooth, WiFi (e.g., IEEE 802.11 and variants thereof), ultrasonic transmission, optical transmission and/or various forms of radio, though the embodiments described herein are not limited thereto. In some embodiments, the communication path 235 may be a wired connection such as, for example, Ethernet, Universal Serial Bus (USB), RS-232, RS-485, Serial Peripheral Interface (SPI), and/or Inter-Integrated Circuit (I2C), though the embodiments described herein are not limited thereto. It will be understood that the communication path between the analytic system 230 and the fluidic sampling apparatus 220, the analytic system 230 may communicate additionally or alternatively, with the physical sensor array 225.

Figure 5A:
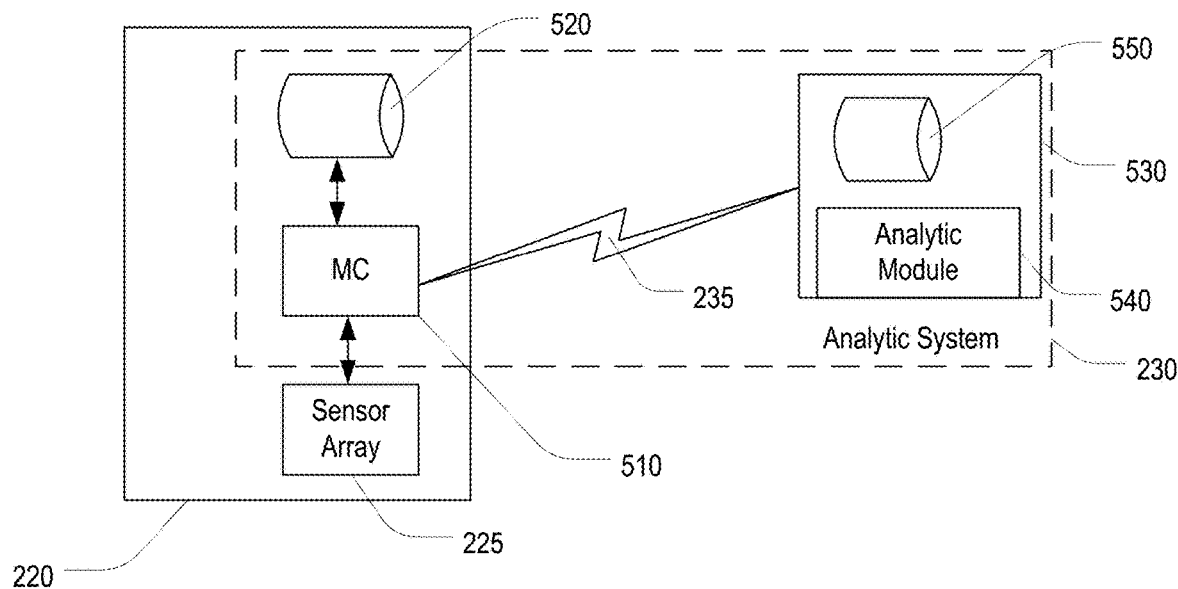
FIGS. 5A and 5B illustrate example embodiments of the analytic system, according to various embodiments described herein.
Figure 5B:
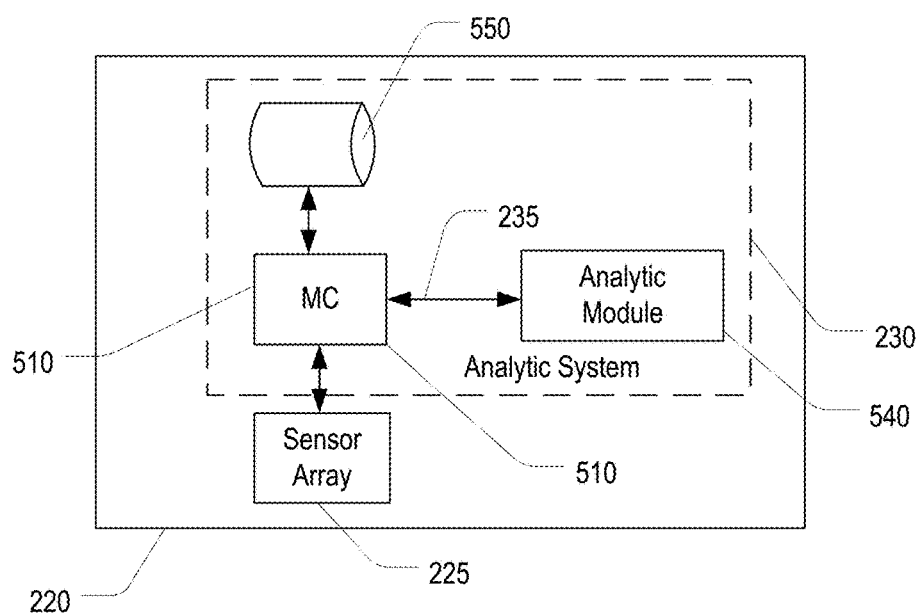

FIGS. 5A and 5B illustrate example embodiments of the analytic system 230, according to various embodiments described herein.

FIG. 5A illustrates an embodiment of the analytic system 230 in which portions of the analytic system 230 are within the fluidic sampling apparatus 220. A portion of the analytic system 230 within the fluidic sampling apparatus 220 may include, in part, a micro-processor controller 510. The micro-processor controller 510 may be, or may include, one or more programmable general purpose or special-purpose microprocessors, digital signal processors (DSPs), programmable controllers, application specific integrated circuits (ASICs), programmable logic devices (PLDs), field-programmable gate arrays (FPGAs), trusted platform modules (TPMs), or a combination of such or similar devices. The micro-processor controller 510 may be configured to execute computer program instructions to perform some or all of the operations and methods for one or more of the embodiments disclosed herein.

The micro-processor controller 510 may be coupled to local storage 520. The micro-processor controller 510 may store data received from the physical sensor array 225 in local storage 520, and may then output the data to external analysis device 530 over communication path 235.

External analysis device 530 may process the data provided from the physical sensor array 225 to further analyze the fermentation process of the fermentation container. The processing of the data may be performed, in part, by analytic module 540 executing on external analysis device 530. Analytic module 540 may be executable code capable of being executed on a processor of the analysis device, and configured to perform operations as described further herein. The external analysis device 530 may include external storage 550. The external storage 550 may store data received from the physical sensor array 225 and/or results from the analysis performed by the analytic system 230. In some embodiments, external analysis device 530 may be a cloud based central processing and storage server.

FIG. 5B illustrates an embodiment of the analytic system 230 in which all or most of the analytic system 230 is contained within the fluidic sampling apparatus 220. The embodiment of FIG. 5B may operate the same or similar as that described with respect to FIG. 5A. However, in the embodiment of FIG. 5B, the operations performed by the external analysis device 530 of FIG. 5A, may be performed by the micro-processor controller 510. Similarly, in the embodiment of FIG. 5B, the analytic module 540 may execute its operations on the micro-processor controller 510.

Though FIGS. 5A and 5B illustrate specific implementations of the embodiments described herein, it will be understood that these are only examples, and other physical implementations of the analytic system 230 are possible without deviating from the scope of the various embodiments herein. For example, FIG. 6 illustrates an example electronic device that can be utilized for the analytic system 230 of the embodiments as described herein.

Figure 6:
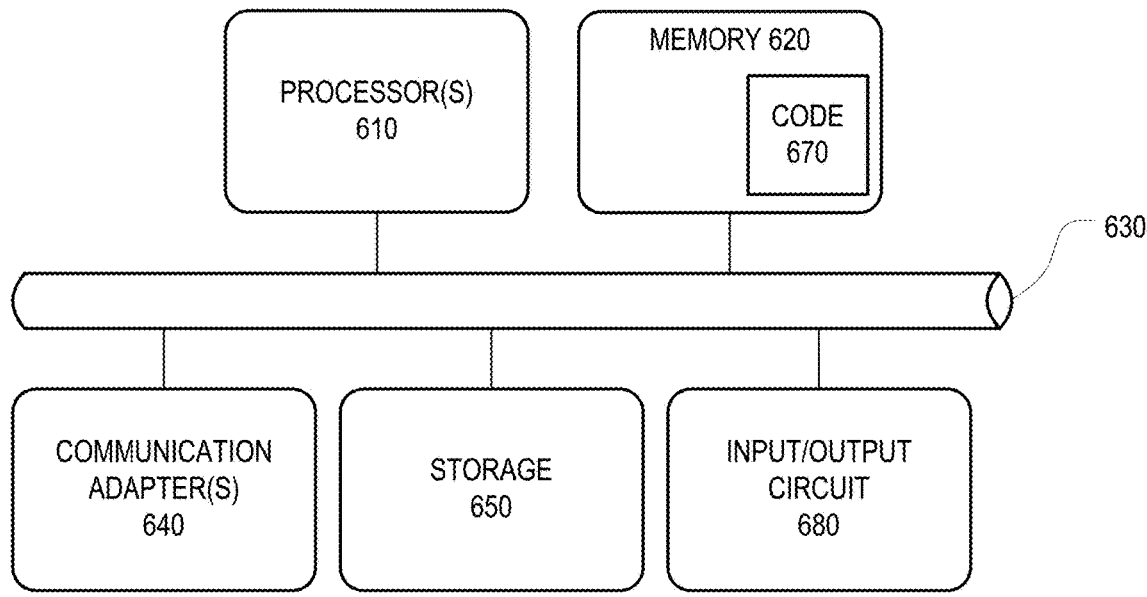
FIG. 6 is a block diagram of an analytic system capable of implementing the methods and operations associated with monitoring a fermentation process, according to various embodiments described herein.

FIG. 6 is a block diagram of an analytic system 230 capable of implementing the methods and operations associated with monitoring a fermentation process, according to various embodiments described herein. The analytic system 230 may use hardware, software implemented with hardware, firmware, tangible computer-readable storage media having instructions stored thereon and/or a combination thereof, and may be implemented in one or more computer systems or other processing systems. The analytic system 230 may also utilize a virtual instance of a computer. As such, the devices and methods described herein may be embodied in any combination of hardware and software. In some embodiments, the analytic system 230 may be part of an imaging system. In some embodiments, the analytic system 230 may be in communication with the physical sensor array 225 illustrated in FIG. 1.

As shown in FIG. 6, the analytic system 230 may include one or more processors 610 and memory 620 coupled to an interconnect 630. The interconnect 630 may be an abstraction that represents any one or more separate physical buses, point to point connections, or both connected by appropriate bridges, adapters, or controllers. The interconnect 630, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

The processor(s) 610 may be, or may include, one or more programmable general purpose or special-purpose microprocessors, digital signal processors (DSPs), programmable controllers, application specific integrated circuits (ASICs), programmable logic devices (PLDs), field-programmable gate arrays (FPGAs), trusted platform modules (TPMs), or a combination of such or similar devices, which may be collocated or distributed across one or more data networks. The processor(s) 610 may be configured to execute computer program instructions from the memory 620 to perform some or all of the operations for one or more of the embodiments disclosed herein. For example, the processor(s) 610 may be configured to execute computer program instructions from the memory 620 to perform the analytic module 540 of FIGS. 5A and 5B.

The analytic system 230 may also include one or more communication adapters 640 that may communicate with other communication devices and/or one or more networks, including any conventional, public and/or private, real and/or virtual, wired and/or wireless network, including the Internet. The communication adapters 640 may include a communication interface and may be used to transfer information in the form of signals between the analytic system 230 and another computer system or a network (e.g., the Internet). The communication adapters 640 may include a modem, a network interface (such as an Ethernet card), a wireless interface, a radio interface, a communications port, a PCMCIA slot and card, or the like. These components may be conventional components, such as those used in many conventional computing devices, and their functionality, with respect to conventional operations, is generally known to those skilled in the art. In some embodiments, the communication adapters 640 may be used to transmit and/or receive data associated with the embodiments for creating the mesh generation described herein.

The analytic system 230 may further include memory 620 which may contain program code 670 configured to execute operations associated with the embodiments described herein. The memory 620 may include removable and/or fixed non-volatile memory devices (such as, but not limited to, a hard disk drive, flash memory, and/or like devices that may store computer program instructions and data on computer-readable media), volatile memory devices (such as, but not limited to, random access memory), as well as virtual storage (such as, but not limited to, a RAM disk). The memory 620 may also include systems and/or devices used for storage of the analytic system 230.

The analytic system 230 may also include one or more input device(s) such as, but not limited to, a mouse, keyboard, camera, and/or a microphone connected to an input/output circuit 680. The input device(s) may be accessible to the one or more processors 610 via the system interface 630 and may be operated by the program code 670 resident in the memory 620.

The analytic system 230 may also include a storage repository 650. The storage repository 650 may be accessible to the processor(s) 610 via the system interface 630 and may additionally store information associated with the analytic system 230. For example, in some embodiments, the storage repository 650 may contain fluid sample data and/or analytics data data as described herein. Though illustrated as separate elements, it will be understood that the storage repository 650 and the memory 620 may be collocated. That is to say that the memory 620 may be formed from part of the storage repository 650.

As illustrated in FIGS. 5A and 5B, the analytic system 230 may execute an analytic module 540 to analyze samples such as those communicated to the analytic system 230 by the physical sensor array 225. The analytic module 540 may be capable of a number of analytic operations, including inferring the internal state of the yeast from the data extracted from the fermentation process of the fermentation container 210, comparing the progress of a given fermentation in real time to a previously established baseline, providing real time estimates of key fermentation process output values such as overall process time, final gravity, and finishing pH, providing warnings when measured fermentation parameters exceed acceptable bounds, and suggesting appropriate steps that can be taken to modulate the course of a fermentation which is not proceeding properly.

The analytic module 540 may include software and/or hardware capable of analyzing the data received from the physical sensor array 225 in use and generating data analysis that includes visualization outputs and end-user notification capabilities.

Unlike conventional systems, embodiments as described herein have the ability to monitor, in near real-time, multiple parameters, at once, selected for their relevance and utility in subsequent analysis, automatically store the data in a purpose built database, and apply algorithms and inference tools from computational molecular biology and information about regulatory networks in a fermentation organism to analyze the course of the fermentation. In some embodiments, a fermentation organism may be a fungus. In some embodiments, a fermentation organism may be a yeast. Example types of yeast that may be analyzed include, but are not limited to, *Saccharomyces cerevisiae, Saccharomyces pastorianus, Saccharomyces bayanus, Brettanomyces Bruxellensis, Brettanomyces Lambicus, Kluyveromyces lactis, Yarrowia lipolytica*, or any combination thereof.

During the fermentation process, the cells of a fermentation organism interact with the environment to sense the conditions, extract nutrients, and metabolize or store these nutrients. As they metabolize nutrients, the cells both deplete their environment of certain molecules while adding other components to it, such as protons or ethanol. The timing of and the rate and level at which these chemical and biochemical changes in the environment take place are parameters that can be observed and which can be taken as proxies for the gene expression programs (regulatory networks) that are activated by the cells of the fermentation organism in response to the environmental conditions that the organism is experiencing.

The timing, level and rate of activation and repression of specific genes can be indicative of the health and performance of a fermentation organism during fermentation. The genes associated with growth and metabolism during fermentation are part of gene expression programs (networks) that control the level of expression of a large portion of the genome of a fermentation organism during fermentation. Regulatory proteins called transcription factors carry out control of gene expression. The transcription factors work to activate or repress clusters of genes, thereby achieving the expression of specific genes at the appropriate times with the appropriate rate and at the appropriate level.

The embodiments described herein incorporate novel gene expression analysis techniques, employed to understand the activity of these transcription factors and how they control gene expression during fermentation. By analyzing and cataloging gene expression during fermentation, and by combining this new information with already available information on gene regulation in a fermentation organism (e.g., yeast), the genes that belong to specific clusters that are temporally regulated during fermentation have been identified. These genes control certain metabolic pathways so that with this background information, the dynamics of chemical and biochemical parameters during a fermentation can be used to infer information regarding the regulation status of specific genes. Furthermore, since these genes are regulated in groups, the activity of many genes can be inferred from the analysis of sensor data. In some embodiments, real-time sensor data may be used to provide an on-going and continuous view of the state of the activity of the fermentation organism.

As an example, maltose is a sugar commonly found in grain extracts that can be metabolized by yeast for energy and ethanol production during an anaerobic fermentation. However, maltose is not an optimum sugar for yeast to consume, as there are other sugars that require less energy to metabolize and are therefore preferentially utilized. Examples of these optimum sugars are the so-called simple sugars—glucose, sucrose, and/or galactose. Maltose uptake and metabolism in yeast is repressed until these other sugars have been exhausted. In fermentation for beer production, the metabolism of maltose by yeast is an indication that simple sugars are depleted. However, to analyze the profile of the sugar content of fermentation substrates is not trivial. Rather than use expensive enzymatic or chromatographic assays to test for the concentration of various types of sugars at various points in the fermentation process, the sensor panel and analytical system in the invention described here uses pH changes, in combination with information about gene regulation as noted above, to indicate the onset of maltose consumption.

As an example, the yeast maltose transporter is a maltose/proton symporter; this means that for every maltose molecule brought into a yeast cell, a proton is also carried into the cell leading to a change in pH of the fermentation substrate that can be detected by chemical sensors. The maltose import machinery does not work in isolation. While this symporter is in operation, other transporters in the cell are actively acidifying the substrate. Therefore, a change in the rate of acidification occurs when the maltose/proton symporter is functioning amidst other biological processes. Once this change has been characterized, the observation of the rate of pH change in the substrate as read by the sensor panel can be used as an indicator that specific maltose transporters are active and that the cells have shifted from using simple sugars and are activating genes to perform less efficient sugar metabolism while turning off genes used in glucose, galactose, and sucrose metabolism. Thus, the relationship between gene expression, sugar metabolism and pH is first characterized, and then pH and other parameters monitored by the embodiments described herein can be used to detect the stages in the fermentation process. Further, the rates of change of each parameter may be analyzed and compared to discover relationships between parameter values and the rate of change of other parameter values, and the relationships between the rates of change of different parameter values.

The information established from the sensors (e.g., the physical sensor array 225 of FIG. 1) allows for monitoring of the physical characteristics/parameters of, for example, beer during fermentation, but it also enables monitoring of fermentation performance by the fermentation organism. The metabolic processes within the fermentation organism are responsible for the changes in chemistry of the fermentation product (e.g., beer) throughout each fermentation run. Fermentation organisms are continually responding to and remodeling their environment during a fermentation. Underlying the metabolic activity of a fermentation organism is a sophisticated control system that senses the environment, interprets the signals, and responds accordingly. This control system is a gene regulatory network comprised of proteins that activate and repress expression in response to the environmental signals and biological needs of the cell of the fermentation organism at that point in time. These networks respond dynamically to the environment during a fermentation and the outputs are dependent upon the integration of many signaling and surveillance systems in the cell that must be processed in context with the other conditions. Properly analyzed and understood, the physical (e.g., biological, chemical, etc.) parameters of each fermentation provide insight into the operation of these networks.

Regulatory networks have been extensively mapped in *S. cerevisiae*. However to understand which regulatory pathways and interactions are operational at any given time, experimental data from metabolically active yeast must be observed and the transcriptional state measured. In at least some embodiments, measurement of the transcriptional state, or measuring the transcriptome, includes assessing the levels of RNA for each gene in the fermenting organism population. This can be accomplished, for example, by sampling the fermentation, isolating the RNA from the substrate, and then purifying the RNA. The RNA can then be measured by fluorescence microarray hybridization, or more commonly, RNA-Sequencing. Collected data is computationally normalized and a value for RNA quantity corresponding to each gene in the fermenting organism is assigned. It is contemplated that this assay is performed for every time point in the fermentation to be analyzed.

To directly detect the interaction of a network with all gene targets is possible, but time and labor intensive. Instead, embodiments as described herein employ quantitative techniques to infer these networks with great accuracy from single time course studies. With these tools, the expression levels of genes may be connected with the proper regulatory networks (RNs) and associated with the biochemistry of fermentation. After mapping these RNs during fermentation, physical parameters collected during a fermentation provide accurate indications of the genes enacting the biochemical pathways and their upstream regulators. The fermentation RN identifies the brewing specific regulatory pathways up to the environmentally responsive sensors sensitive to the fermentation environment. Mapping input, to control system, to output, information from the device allows the user to understand what conditions should be adjusted to give a desired result. Therefore, directed, specific control of the conditions within a fermentation can change the fermentation performance in a predictable and reproducible manner.

Figure 7:
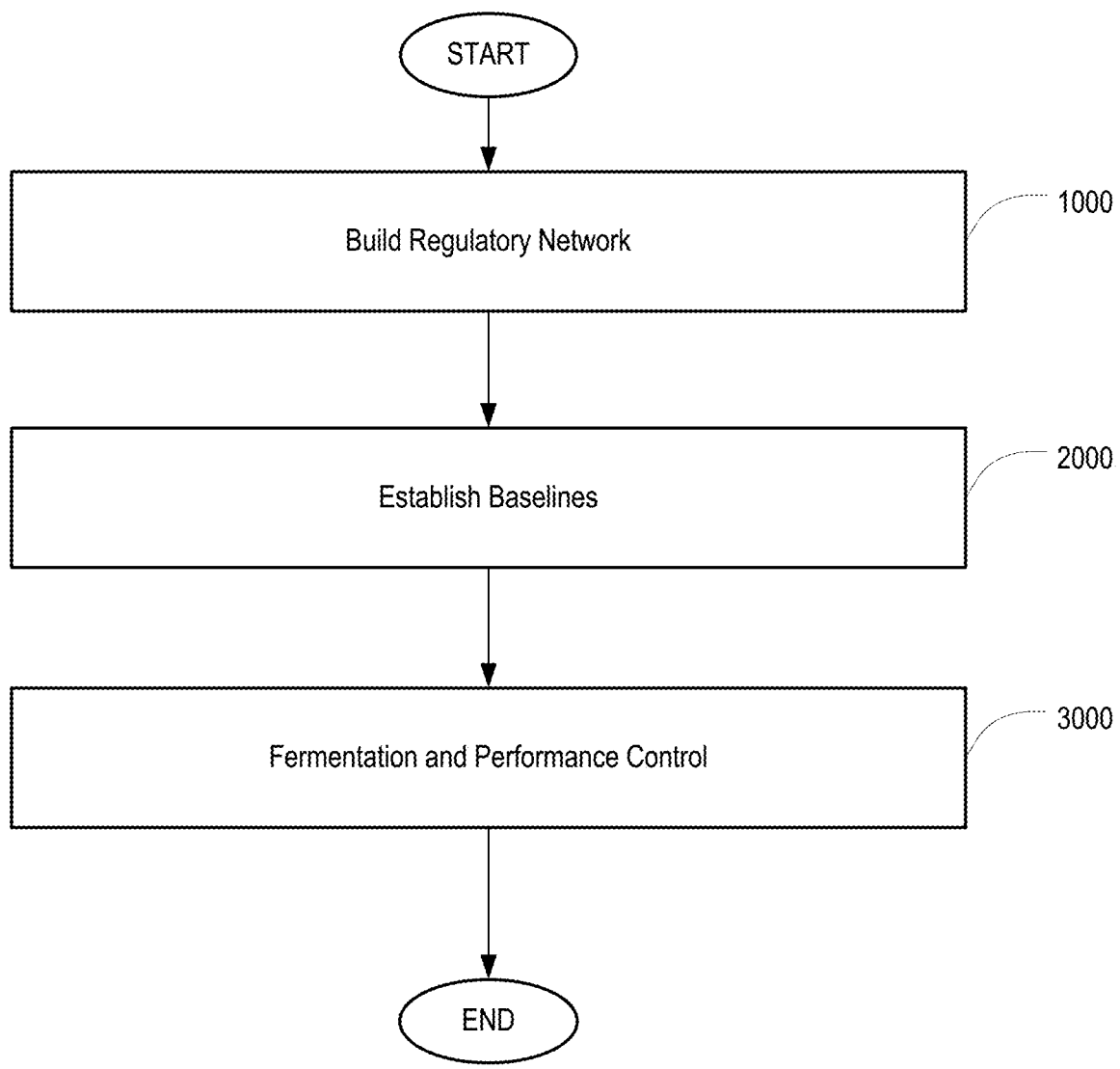
FIG. 7 illustrates monitoring the performance of a fermentation organism in fermentation systems, according to various embodiments as described herein.

FIG. 7 illustrates monitoring performance of a fermentation organism in fermentation systems, according to various embodiments as described herein. As illustrated in FIG. 7, the operations may begin with block 1000, for building a regulatory network for the fermentation organism.

Figure 8:
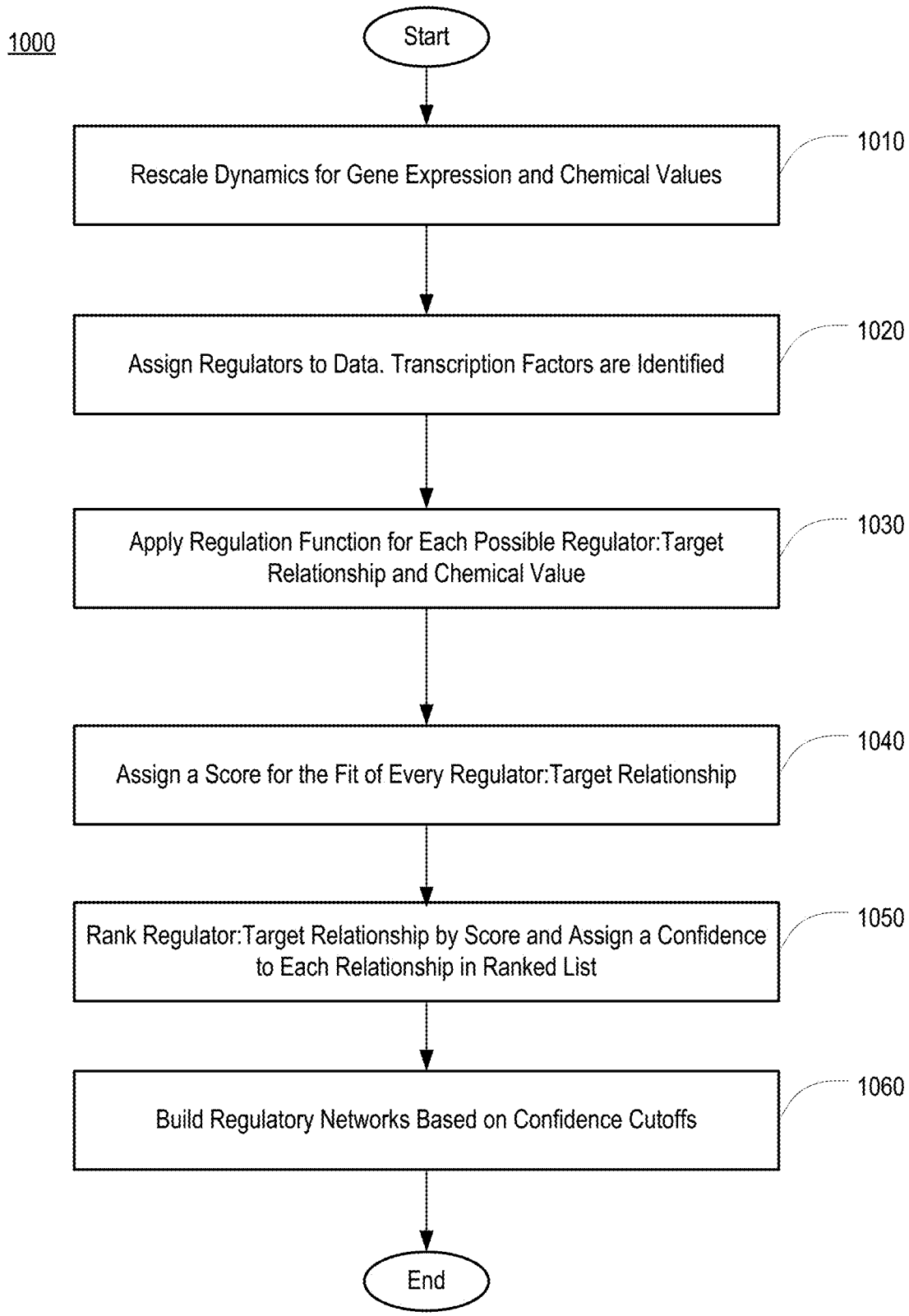
FIG. 8 illustrates a method for forming a database of regulatory networks for a fermentation organism, according to various embodiments as described herein.

FIG. 8 illustrates forming a database of regulatory networks, according to various embodiments as described herein (block 1000). Standard Gene Expression data from microarray or RNA-sequencing platforms, along with sensor data from fermentation may be handled in using the method illustrated in FIG. 8. Such a process may utilize a computational cluster with parallelizable compute cores and local storage for pipeline analysis results, and may utilize next generation sequencing and/or microarray data collected from a fermentation run during which physical parameters were observed by the sensor panel. Gene expression data may be summarized and normalized using transcriptomics standard operating procedures and quality control measures. As illustrated in FIG. 8, forming a database of regulatory networks for a fermentation organism may start with block 1010 to rescale dynamics for gene expression and chemical values. In this operation data may be rescaled from 0-100 for each dynamic value (chemical parameter measurement or gene expression). Data may be filtered so that only dynamic parameters and gene expression values are considered for analysis. Using public databases, and a proprietary database of transcription factors, the dynamic gene expression values that correspond to the transcription factors may be identified and marked as possible regulators (block 1020). Using a suite of modeling software, the gene expression of all targets, both gene expression and chemical values may be compared to the gene expression of identified regulators (block 1030). All possible regulator-target relationships may be scored (block 1040) and then ranked by their scores (block 1050). The output may be a regulatory network including transcription factors capable of regulating the dynamics in gene expression and chemical parameters throughout a fermentation (block 1060). These models allow for regulatory and co-regulatory relationships between genes and chemical parameters to be identified.

In block 1020, regulators may be assigned to data. Transcription factors may be identified in this step. The genomic annotation for gene regulators (activators and repressors of gene expression) may be identified through previous experiments, gene domain discovery, and evolutionary orthology.

In block 1030, the operations may apply a regulation function for each possible regulator: target relationship and/or parameter value. Local connections between regulators and downstream gene targets and chemical change targets may be assessed. These connections are not determined by curve matching or autocorrelation where only the shapes of the curves are considered and the most similar curves are matched. Instead, the curve of the regulator may be translated by a function using biologically plausible parameters to test whether it can generate the output, in this case a target gene or chemical change. The framework considers the function $f(R)=T$ where R is a regulator with the ability to repress or activate T by the function $f$ The function $f$ may contain multiple parameters derived from real world values to explain the kinetics of regulatory relationships in a biological system. For each target T, every potential regulator R may be tested and a likelihood model is used to obtain an optimum set of parameters for each particular potential relationship.

In block 1040, the operations may assign a score for the fit of each regulator: target relationship. For each target T, each potential $f(R)=T$ may then be compared to find the best regulatory relationship that explains the target T. For this, models that best fit the real data may be fed into the pipeline, and models that demonstrate the robustness inherent in biological systems may be favored in a probability distribution output of N regulators for each target, where N is twice the number of R when each regulator is tested as an activator and repressor of T.

In block 1050, the operations may rank regulator: target relationships by score, and may assign a confidence to each relationship in a ranked list. Based on density of data and user input, confidence thresholds may be put in place for the strength of local interactions computed in block 1020 and 1030. From the local interactions that satisfy this cutoff, larger networks representing the underlying biology of the interaction may be constructed.

In block 1060, the operations may build regulatory networks based on confidence cutoffs formulated in block 1040. The gene expression network may be graphically represented along with the chemical value plots for each fermentation. The coincidence of gene expression and parameter changes as measured by the physical sensor array 225 (e.g., FIG. 1), as well as the regulatory relationships between genes, can be viewed in this way.

An example of building a gene regulatory network using a method known as a Local Edge Machine (LEM) will now be discussed. The LEM process is provided only as an example, and it will be understood that other methods, including various types of statistical analysis associated with the underlying genes being tracked, will be apparent to those of ordinary skill in the art without deviating from the embodiments described herein.

Given a set of genes deemed to be potentially important for network function, LEM takes a Bayesian approach to answer the following question: of all possible regulators, which regulator and regulatory logic (activation or repression) best models the expression dynamics of each gene? The LEM algorithm may mode the gene expression of each node and may score each possible regulation in the network.

Consider a gene regulatory network with a set of N nodes, $=\{X1, \ldots, XN\}$. For $i=1, \ldots, N$, $X_i(t)$ denotes the expression level of gene $X_i$ at time t. The data, denoted by D, consist of the observed expression levels of the N nodes at T time points, $\{t_j\}Tj=1$.

According to one model, the data are generated according to a system of ordinary differential equations (ODEs), possibly observed with noise. More specifically, for the target $X_i$, a model is that $X_i$ satisfies $$\frac{dX_i}{dt} = \alpha_i f_i(X(t)) - \beta_i X_i(t) + \gamma_i, \qquad (1)$$

where $X(t)=(X_1(t), \ldots, X_N(t))$, the function $f_i: \mathbb{R}^N \to \mathbb{R}$ governs the type of regulation that $X_i$ experiences, $\alpha_i > 0$ represents the strength of the regulation, $\rho_i \geq 0$ represents the rate of degradation of $X_i$, and $\gamma_i \geq 0$ represents the basal rate of production of $X_i$. In general, stochastic effects may play a significant role in the dynamics of any individual cell, and such considerations lead one to stochastic differential equations. However, the data may be generated by averaging expression levels over many ($\sim 10^8$) individual cells, and one, therefore, may assume that the stochastic effects are insignificant, leading to the use of ODEs.

Hill function kinetics may be used to model activation and repression of the target node. Equations of this type are not intended to model each individual aspect of regulation explicitly. Rather, they are intended to subsume multiple levels of regulation (e.g., translation, transcription, chromatin modification, direct binding, etc.) into a single equation with relatively few parameters. In general, one expects biological networks to be sparse, and even in cases where this assumption is broken, the method may seek to identify the most dominant components of a regulation in a given experimental condition. Thus, regulatory functions $f_i$ of the following forms may be considered, which correspond to regulation by a single gene:

$$f_i(X) = \begin{cases} \dfrac{X_j^{n_i}}{K_i^{n_i} + X_j^{n_i}} & \text{(activation by } X_j\text{),} \\ \dfrac{K_i^{n_i}}{K_i^{n_i} + X_j^{n_i}} & \text{(repression by } X_j\text{).} \end{cases} \quad (2)$$

More complex regulatory functions $f_i$ could be allowed in the model class if the goal is to infer simultaneous regulation by multiple genes. However, attention may be restricted to single regulation, since the information content of time-series datasets at present appears not to support the substantial increase in complexity of the model class that would result from inclusion of combinatorial regulation.

Thus, to specify a system of ODEs completely, as in Equation 1, included herein, for each node $X_i$, one may select a regulator $X_j$, a type of regulation (activation or repression), and a vector of real-valued parameters ($\alpha_i, n_i, K_i, \beta_i, \gamma_i$). Triples of the form ($X_i, X_j$, a) or ($X_i, X^j$, r) may be referred to as edges, where ($X_i, X_j$, a) may be interpreted as the relationship that $X_i$ is activated by $X_j$ and ($X_i, X^j$, r) may denote that $X_i$ is repressed by $X_j$. Note that these edges are both signed and directed.

The LEM inference method first involves making a local approximation, which allows one to infer the regulation of each node separately, rather than all at once. To infer the regulation of the target X (here the subscript i is dropped from the above notation without introducing ambiguity), LEM takes a Bayesian approach that utilized the Gibbs posterior principle and a Laplacian approximation in the computation of the posterior distribution.

In general, if M is a model (among several) and D is a dataset, then Bayes' rule yields a posterior probability of M given the data D:

$$p(M \mid D) = \frac{p(D \mid M)\pi(M)}{p(D)} \propto p(D \mid M)\pi(M).$$

Here p(D|M) is the likelihood of the data D given the model M, π is a probability distribution on the possible models, called the prior distribution, and p(D) is the likelihood of D (averaged over all the possible models). If one interprets the prior distribution as a belief in the veracity of each model prior to generation of the data, then the posterior distribution represents the optimal way to update the belief in light of the data. If M requires an additional choice of parameter θ to be a fully generative model, the posterior distribution may be written as an integral over θ:

$$p(M|D) \propto \int p(D|M,\theta)\pi(M,\theta).$$

For LEM, the edge inference problem may be formulated in a similar manner. Let X be a fixed node and E an edge with X as the target [i.e., E=(X,Y,a) or E=(X,Y,r) for some node Y]. One may view E as a model for explaining the behavior of X and employ the Bayesian framework above to compute its posterior probability. To do so, a prior distribution on the set of possible models may be specified, which in one case is the set of possible edges with X as the target, and a likelihood function may be used. Recall that in this model, each edge utilizes an additional choice of parameter vector $\theta=(\alpha, \beta,\gamma,n,K)$ (as in Equations. 1 and 2) in order to specify fully the corresponding differential equation.

The prior distribution may be set by the user, and there are many opportunities for integrating other data types in this manner. However, according to embodiments as described herein, the prior distribution may be set as follows. First, let π(E) be the uniform distribution over the possible edges that have X as a target. For each edge E with X as the target, select a priori bounds on each of the parameters in $\theta_E$, resulting in a region $R_E$ (contained in $\mathbb{R}^5$) of biologically reasonable parameter values. Once these bounds are selected, one may choose the maximum entropy prior distribution subject to these bounds, which is the least informative prior on $R_E$ and ensures that the result is not unnecessarily biased. This distribution is $$\pi(E, \theta) = \frac{1}{s \cdot \text{Vol}(R_E)},$$

where s is the number of edges with X as target and Vol($R_E$) is the volume of $R_E$.

With the prior distribution set, attention may be turned to the likelihood. In fact, as different experimental protocols could lead to significantly different noise models, each of which is likely to be difficult to determine accurately and precisely, one may proceed under the assumption that one does not have access to a likelihood function. In such cases, the Gibbs posterior principle states that the optimal method for updating one's beliefs in light of the data is to replace the likelihood p(D|M,θ) by $$\exp(-\ell(D,E,\theta)),$$

where $\vartheta$(D,E,θ) is an appropriately chosen loss function. A loss function $\ell$(D,E,θ) may be specified as follows. For a triple (D,E,θ), define the function F: $[t_1, t_T] \to \mathbb{R}$ on the points $\{t_j\}_{j=1}^{T}$ by $$F(t_j) = \alpha f(X(t_j)) - \beta X(t_j) + \gamma,$$

and then extend F to the whole interval $[t_1, t_T]$ by linearly interpolating between these values. That is, if $t = u t_j + (1-u)t_{j+1}$ for some j<T and u∈(0,1), then let $F(t) = uF(t_j) + (1-u)F(t_{j+1})$. Now set $$\hat{X}(t) = \int_{t_1}^{t} F(s)\,ds,$$

and define the loss $\vartheta$(D,E,θ) to be the mean squared error between the observed values $\{X(t_j)\}_{j=1}^{T}$ and the properly shifted model prediction $\{\hat{X}(t_j)\}_{j=1}^{T}$:

$$\ell(D, E, \theta) = \min_{c \in \mathbb{R}} \frac{1}{T} \sum_{j=1}^{T} \left(X(t_j) - \hat{X}(t_j) - c\right)^2.$$

This choice of loss function is effectively equivalent to the choice of a Gaussian noise model.

With the prior distribution and the loss function now specified, the (marginal) Gibbs posterior probability of the edge E given the data is $$p(E \mid D) \propto \int_{R_E} \exp(-\ell(D, E, \theta)) \frac{d\theta}{s \cdot Vol(R_E)}. \quad (3)$$

As is common in many Bayesian methods, the above integral does not have a closed-form solution. A Laplace approximation may be chosen to estimate it. From this approximation, one can see that LEM explicitly favors networks whose dynamics are more robust to a perturbation in the parameter space. In principle, one could attempt to compute other approximations of this integral, including Monte Carlo approximations. However, the Laplace approximation has been found to be computationally fast and produces sufficiently accurate results for the purposes of the embodiments described herein.

Thus, the output of LEM may be N different probability distributions—one for each node in the network. The distribution for node X may be interpreted as representing which edge is the dominant regulatory interaction (edge) controlling the expression of X There are multiple ways to obtain a single network from this set of distributions, the simplest of which is to select the most likely edge from each distribution.

Referring again to FIG. 7, once the regulatory network has been formed, monitoring performance of a fermentation organism in fermentation systems may continue with operation 2000 to establish baselines.

For some fermentation systems, such as beer, the end user has target values in mind for many of the physical parameters (e.g., chemical, biological, etc.) of the substrate. Continuous monitoring of these parameters, such as pH, density/gravity (as an indirect measure of ethanol), and dissolved oxygen may allow an end user to detect when the fermentation reaches particular milestones. The rate at which these targets are reached is an indicator of the health and performance of a fermentation organism. As these values are monitored continuously, the rate and values are both determined and used for analysis. The fermentation substrate is complex and often specific to a particular fermentation process or fermentation product (e.g., a brewery, beer).

Therefore, best practices with the sensor panel and associated analytical tools may include establishing acceptable baseline fermentations (and their associated parameters) by monitoring a series of fermentations and identifying the acceptable and unacceptable fermentation performances. The baseline performance threshold may be set by the ensemble performance of the acceptable fermentations. Such a calibration may allow the end user and the analytical pipeline to identify the normal parameter values, rates of change, and the relationships between parameters that occur during a normal fermentation.

The establishment of this baseline will allow intervention into fermentations that fall outside of acceptable parameters. Several example interventions are provided below:

Example 1

If density/gravity readings do not correlate with appropriate changes in pH during a fermentation, it may indicate that the fermentation organism that is consuming the substrate may not be acidifying the substrate. This is due to the fact that the regulatory networks discovered in the fermentation organism species are constrained by the type of outputs they can create and how the parameters must change. The regulatory networks regulate gene expression programs that, for example, consume the substrate but also acidify the substrate at a particular rate. If the parameter values indicate a deviation from the type of relationship between parameters observed under normal fermentation conditions using this fermentation organism species, then there may be evidence that another biological regulatory network is at play during the fermentation. This is a strong indication of microbial contamination with another microorganism with a different set of regulatory network relationships and constraints. This batch should be discarded and the fermenter vessel cleaned. In the case of a bioethanol production run, the substrate could be heated to destroy the contamination and re-inoculate with yeast to initiate a corrected fermentation run.

Example 2

When initial oxygen levels (within the first hour of a fermentation) are not high enough to provide a fermentation organism with the molecular oxygen needed for proper growth, oxygen may be added within the first several hours to improve proliferation and fermentation performance of the fermentation organism.

Example 3

If pH levels do not drop, for example, within the first 24 hours, this may indicate poor health of a fermentation organism. To aid the organism with fermentation and to make conditions inhospitable for some potential contaminants, acids may be added. Depending on the fermentation, organic acids such as lactic acid or inorganic acids such as phosphoric acid, hydrochloric acid, or sulfuric acid can be added to the fermentation substrate for acidification. Fermentation performance by yeast, for example, is optimal in low pH ranges (approximately 3.5-4.5).

Example 4

Increases in pH and dissolved oxygen levels at a late stage in a fermentation process could indicate a die off of yeast due to alcohol intolerance. In some embodiments, a late stage of the fermentation process may be a stage after the bulk of sugars have been consumed, and/or the density is within approximately 15% of the finishing parameter values. Certain vitamins and antioxidant compounds can be added to the substrate at this point. These vitamins may be readily taken up by a fermentation organism to help mitigate further die off and promote fermentation performance. The addition of vitamins and antioxidant compounds at earlier points in the process may not be effective, as they are simply metabolized.

A database, such as the data storage 650 of the analytic system 230 (see FIGS. 1, 5A, 5B, and 6) may store the data and can be used for analysis of:

the particular fermentation in question compared to other fermentations of the same product, by the same company (or in the same facility);

the particular fermentation in question compared to fermentations of similar products by other fermentation companies or at other sites producing the same product;

the particular fermentation in question compared to other fermentations of other products produced by the same company;

the particular fermentation in question compared to other fermentations of other products by others; and other similar comparisons between products produced at the same or different facilities or by different companies.

The database, in turn, may provide deeper insight into the performance and fermentation by a fermentation organism, using customized algorithms capable of discovering relationships among the parameters involved.

In some embodiments, baselines for a particular end user may be adopted from another set of fermentation processes. That is to say, the monitoring system may not necessarily require that baselines be established for specific equipment before performance monitoring can be accomplished. In some embodiments, baselines from similar equipment, similar brewing practices, and/or similar brewing procedures may be adopted by the monitoring system.

Referring again to FIG. 7, once one or more baselines have been established, monitoring in fermentation systems may continue with operation 3000 to perform fermentation and performance control on subsequent fermentations.

Figure 9:
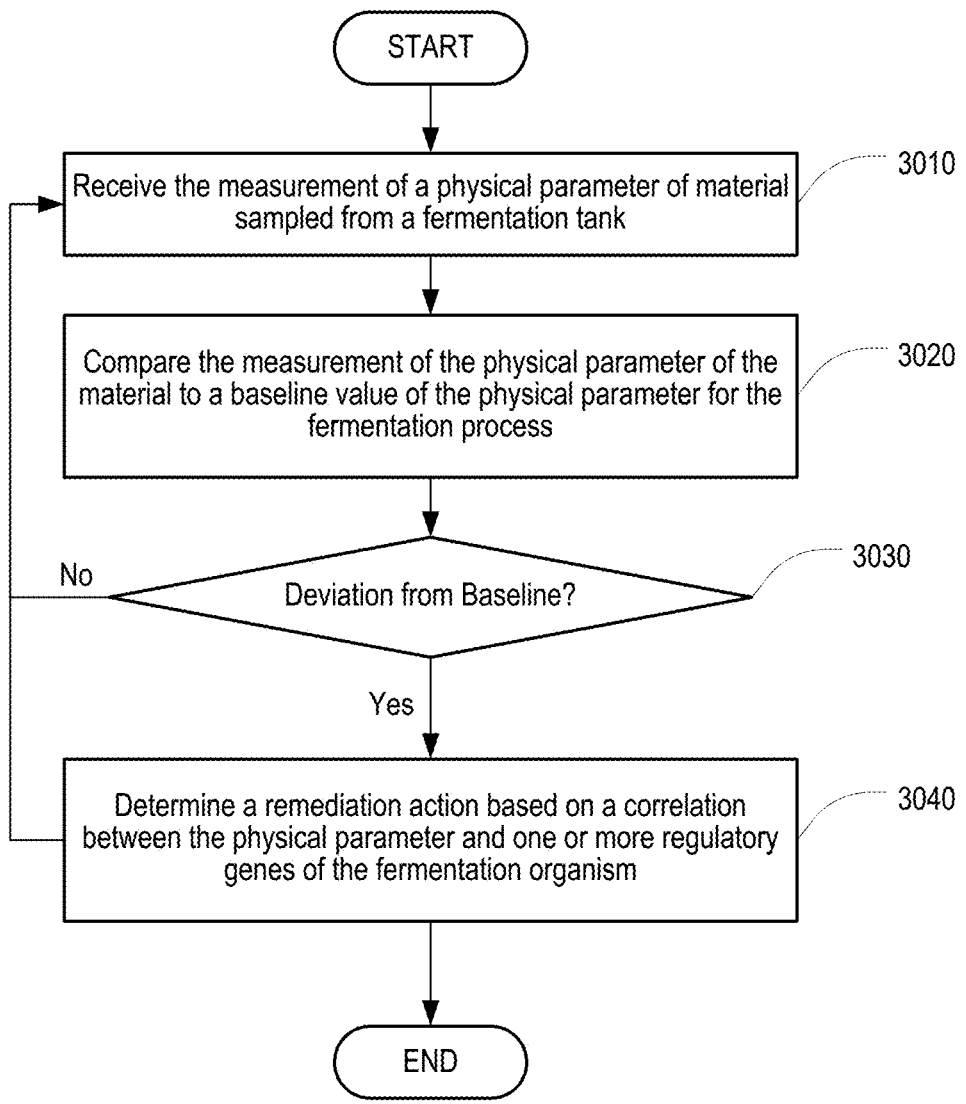
FIG. 9 illustrates fermentation and performance control, according to various embodiments as described herein.
Figure 10:
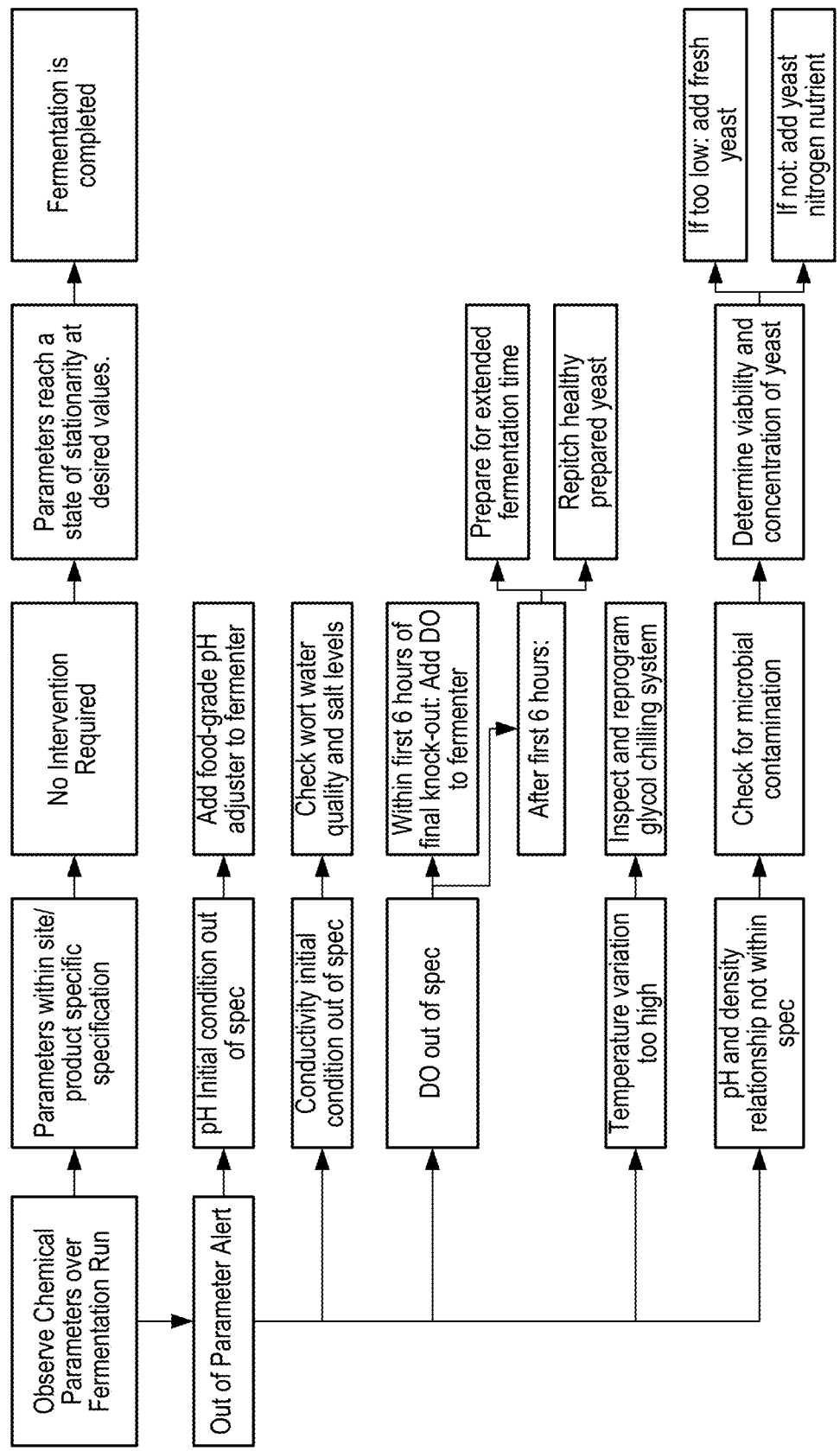
FIG. 10 illustrates an example of the process illustrated in FIG. 9.

FIG. 9 illustrates fermentation and performance control, according to various embodiments as described herein (FIG. 7, block 3000). As illustrated in FIG. 9, methods, systems, and computer program products can include receiving the measurement of the at least one physical parameter of the material sampled from the fermentation tank (block 3010), comparing the measurement of the at least one physical parameter (e.g., chemical, biological, etc.) of the material sampled from the fermentation tank to a baseline value of the at least one physical parameter for the fermentation process (block 3020), comparing the physical parameter to a baseline value (block 3030), and responsive to a deviation of the measurement of the at least one physical parameter of the material sampled from the fermentation tank from the baseline value, determining a remediation action based on a correlation between the at least one physical parameter and one or more regulatory genes of the fermentation organism (block 3040). FIG. 10 illustrates an example of the process illustrated in FIG. 9.

As illustrated in FIG. 10, the sensor data, as interpreted by the pipeline, may aid the operator in making decision on process control that are rooted in understanding the biological interplay between yeast and the fermentation substrate. The flow chart of FIG. 10 describes potential interventions based upon the results output from the invention.

The sensor data (e.g., physical parameters of the fermentation substrate) may be interpreted by the pipeline and compared against the established baseline. The dynamics of the physical parameters are compared and an estimated time of completion for the fermentation is provided within the first 24 hours of fermentation.

The sensor data may be continuously tested for stationarity during a fermentation. When dynamic changes in physical parameters are complete and the yeast is no longer modifying the environment and converting carbon sources to ethanol. In such a case, the operator may be alerted that the fermentation is complete.

In the event that the fermentation does not perform to specification, the sensor data as interpreted by the platform may provide information that the operator may use to make decisions on interventions and process control decisions. Out of parameter alerts may be provided when such events occur. The flow chart of FIG. 10 describes suggested example courses of action dependent on the alert.

For example, if pH alert occurs at the onset of fermentation, a food grade acid or base can be added to the fermentation vessel to adjust the pH back to specification. This may allow for the regulatory network that exists within the fermenting organisms to receive the proper signaling that the conditions are optimized for the particular fermentation. The organisms' regulatory networks then signal to the proper outputs so that the fermentation performance is maximized. The amount to be added and the desired pH level may differ based on time of fermentation. The type of acid or base depends on the product being made.

For example, if the dissolved oxygen (DO) is out of specification, the course of action may also be dependent upon the timing of fermentation.

If the DO is too low, then, if the fermentation is within the first about 6 hours, this is the interval during which added oxygen may aid the fermentation and it should be added to the fermentation.

If the fermentation is after the first about 6 hours, oxygen can have a detrimental effect on ethanol production and should not be added. The operator should expect a longer fermentation time. In some embodiments, if available, the operator may choose to add fresh yeast that has been oxygenated prior to introduction into fermentation vessel.

If the DO is too high, the operator should take note and adjust the process SOP (standard operating procedure) to reduce oxygen supply to the fermentation for subsequent fermentations to save on cost and materials.

For example, the relationship between density of the fermentation substrate and pH may indicate the performance of the fermentation organism, e.g., yeast, in the conversion of the substrate carbohydrate sources to a product, e.g., ethanol.

If the relationship between pH and density falls outside the parameter specification determined by the baseline, microbiology techniques may be used to determine if contaminating organisms are present in the fermentation. If contamination levels are deemed too high, fermentation may be stopped and the equipment cleaned.

If pH can be corrected, the operator may consider adding food grade acids or base to bring pH back into an optimal window for fermentation performance.

If minimal contamination exists, or if the concentration of viable, vital cells of a fermentation organism is too low, the operator can consider outcompeting other microbes by adding further of the fermentation organism, e.g., fresh yeast.

If addition of yeast is not possible, the operation may consider addition of yeast extract to increase available nitrogen for yeast.

For example, conductivity provides an indication of the ions present in the fermentation substrate. If the fermentation substrate shows an initial conductivity reading that is lower than targeted as per the specification, the operator could check with the operator's water supplier to determine if water chemistry profile has changed. The operator could also consider adding specific salts that contribute to the typical water profile used for the specific product/facility, such as calcium salts, magnesium salts, and/or sodium salts. The operator could also consider adding electrolytes that contribute to the health of the yeast to achieve higher fermentation performance, such as zinc salts, manganese salts, and/or copper salts.

If the conductivity reading suggests an ion concentration that is too high, the operator could check with water supplier to determine if water chemistry profile has changed. The operator could also consider reverse osmosis filtration or other means of removing ions from the fermentation substrate water.

For example, temperature may affect the fermentation performance of a fermentation organism. The optimum temperature of a fermentation substrate is highly dependent on the particular fermentation organism or the strain or species of fermentation organism, or desired sensory compound output. Thermostat controlled glycol (or other coolant) temperature control systems typically control fermentation substrate temperature. However, temperature variation within a fermentation can have a negative effect on fermentation performance by a fermentation organism. If large variations in fermentation temperature occur, the operator could consider adjustment upper and lower bounds on thermostat. For fermentations that demand tighter temperature control, the operator could consider utilization of other fermenters within facility with improved temperature control. The operator could also consider changes in heating/cooling system to better match the needs of the facility As described herein, the analytic system 230 may make continuous samples of data from the fluidic sampling apparatus 220. The data may represent samples of the physical parameters of the medium in the fermentation container 210 as sampled by the physical sensor array 225. The analytic system 230 may utilize an analysis suite, such as the analytic module 540 (see FIGS. 5A and 5B), to analyze the samples.

The analysis suite may be built upon a custom database that acquires and stores the real-time data as it is uploaded to off-site servers (at intervals from 1 second to 10 minutes depending on network bandwidth and connectivity).

The purpose of real-time monitoring is to ensure that the fermentation proceeds according to expectations and previously established baselines. The brewer or fermentation supervisor can also access the information electronically using a Graphical User Interface (GUI). From this GUI, the end user will be able to monitor data from the fermentation in near real-time (as it is uploaded). Prior to each fermentation, the end user has the opportunity to add parameters for each of the sensor outputs. If the readings from the sensors on a fermenter fall outside a set parameter range, the unit will alarm and send an alert SMS, email, or other notification to the client of the out-of-parameter value. This is especially useful for facilities that are not manned 24 hours a day or 7 days a week.

The information from each monitored fermentation may be stored and organized in the database by customer, product type or style (in beer and beverage industry), starting nutrient levels, ethanol targets, fermentation duration targets, and/or other metadata that the client desires to use to organize their fermentations within their account. Customer information may be securely protected.

In some embodiments, the present invention provides a method for constructing a baseline database for a selected fermentation process by a fermentation organism in a fermentation substrate, the method comprising: (a) measuring a physical parameter at multiple time points during the selected fermentation process from initiation to termination of the selected fermentation process, thereby providing values (or a rate of change) for the physical parameter over time for the selected fermentation process; (b) measuring a transcriptome of the fermentation organism at the same time points during the fermentation process as measured for the physical parameter to produce a gene expression database over time for the selected fermentation process; (c) inferring regulatory networks of the fermentation organism from the gene expression database; and (d) identifying one or more regulatory genes of the fermentation organism that are correlated with a value or range of values (or a rate of change) for the physical parameter measured for the selected fermentation process, thereby constructing the baseline database for the selected fermentation process that provides a predetermined value or range of values (or predetermined rate of change) for the parameter that is correlated with the one or more regulatory genes of the fermentation organism.

Also provided is a baseline database constructed by the methods of the invention.

In some embodiments, a method of standardizing a selected fermentation process by a fermentation organism in a fermentation substrate is provided, comprising: (a) measuring a physical parameter at multiple time points during the selected fermentation process from initiation to termination of the selected fermentation process, thereby providing values (or a rate of change) for the physical parameter over time for the selected fermentation process; and (b) comparing values (or a rate of change) of the physical parameter measured for the selected fermentation with predetermined values (or predetermined rate of change) for the same physical parameter provided by the baseline database, (c) modifying a fermentation condition to increase or decrease the expression of one or more regulatory genes (i.e., decrease or increase repression or activation of the one or more regulatory genes) of the fermentation organism identified in the baseline database as correlated with the physical parameter when the values (or the rate of change) of the physical parameter measured for the selected fermentation process fall outside the predetermined range of values (or the predetermined rate of change) for the same physical parameter, thereby modifying/adjusting the values (or the rate of change) for the physical parameter so that they fall within the predetermined range of values (or the predetermined rate of change) of the baseline database and standardizing the selected fermentation process.

In some embodiments, measuring a physical parameter at multiple time points comprises measuring the parameter at least every 15 seconds to every five minutes from initiation to termination of the selected fermentation process.

In some embodiments, the physical parameter that is measured may include, but is not limited to, dissolved oxygen level, ethanol level, pH, $CO_2$ level, density, gravity, cell concentration and/or electrical conductivity.

In some embodiments, the fermentation organism may be any organism that is capable of fermentation, including, but not limited to, a fungus, a bacteria, or an algae (e.g., microalgae). In some embodiments, the fermentation organism may be any yeast or any combination of different yeast species or different yeast strains. In some embodiments, the yeast may be *Saccharomyces cerevisiae, Saccharomyces pastorianus, Saccharomyces bayanus, Brettanomyces Bruxellensis, Brettanomyces Lambicus, Kluyveromyces lactis, Yarrowia lipolytica*, or any combination thereof.

In some embodiments, the one or more regulatory genes may be a transcription factor. Any transcription factor known or later identified to be present in a fermentation organism may be used. In some embodiments, a transcription factor useful with this invention may include, but is not limited to, OAF1, PDR3, HIR1, HAP3, RTG3, REB1, NRG2, TEC1, SMP1, HPC2, THI2, MAL33, KAR4, HCM1, RDS1, RPN4, MBP1, PHO2, UGA3, LYS14, NRG1, PDC2, GIS1, INO2, SWI5, UME6, UPC2, ADR1, MET32, YAP6, MTH1, SUM1, ARO80, CAD1, YHP1, STP1, GCN4, MIG3, GLN3, ACA1, DOT6, FLO8, SWI4, SPT2, RPH1, GAT1, HAC1, CDC14, PHO4, PDR1, MIG1, AFT1, HSF1, TOS8, SUT1, CUP2, GTS1, IME4, MIG2, HAP2, RTG2, FZF 1, RME1, MGA1, MAL13, YAP5, OPI1, RIM101, STP2, RSC30, STE12, NDT80, STB5, RPN10, SKN7, CST6, XBP1, FKH1, IMP2, GAT4, MET28, YAP5, DAL81, MGA2, ZAP1, SIP4, GZF3, CBF1, IME1, RSF2, HMS2, BYE1, PUT3, SPT23, IXR1, RGT1, PHD1, MSN4, HAP4, ABF1, ASH1, DAL80, BAS1, GAT3, PPR1, CHA4, ACE2, RFX1, SWI6, IFH1, ECM22, HAP1, PDR8, STP3, SFP1, LEU3, YAP1, YOX1, GAL80, WAR1, ARG81, SOK2, MAC1, MSN2, ARG80, MCM1, MOT5, MSS11, HOT1, RGM1, CAT8, ELP6, CRZ1, FKH2, MET4, SKO1, GCR2, SPS18, RAP1, GIS2, DAL82, YAP7, RTG1, HAL9, INO4, MSN1, CIN5, HMS1, HIR2, AZF1, SFL1, YRR1, YRM1, TYE7, HAP5, PIP2, NDD1, RDR1, MET31, GCR1, RLM1, RDS2, UME1, CUP9, AFT2, GAL4, MDL2, HAA1, YPR015C, ROX1, RDS3, FHL1, ARR1, or any homologue thereof (see, e.g., YEASTRACT database; Teixeira et al. Nucl. Acids Res., 42(D1) D161-D166 (2014)).

In some embodiments, a physical parameter that may be measured can be the density of the fermentation substrate and the one or more genes that correlate with density may include, but are not limited to, ADH1, ADH3, ADH4, ADH5, PDC1, PYK1, ENO1, PGM1, PGK1, TDH1, any homologue thereof, or combination thereof. If the density physical parameter is too low, additional fermentable sugars may be added to the substrate. If the density physical parameter is too high, additional water and yeast may be used to dilute out the fermentable sugar and return density to the desired value.

In some embodiments, a physical parameter that may be measured can be the pH of the fermentation substrate and the one or more genes that correlate with pH may include, but are not limited to, PMA1, CAN1, PDR12, ALP1, any homologue thereof, or combination thereof. If the pH is too high, food grade acids may be added to the fermentable substrate until the target pH is achieved. If the pH is too low, food grade basic chemicals may be added to the fermentable substrate until the target pH is achieved.

In some embodiments, a physical parameter that may be measured can be the conductivity of the fermentation substrate and the one or more genes that correlate with conductivity may include, but are not limited to, PMA1, ENA1, NHA1, TRK1, TRK2, TOK1, PMR1, PMC1, CCH1, MID1, ZRT1, ZRT2, any homologue thereof, or combination thereof. If the conductivity of the fermentable substrate is too high, additional water, yeast, and fermentable sugar may be added to reduce the electrolyte concentration of the solution. If the conductivity of the fermentable substrate is too low, additional food grade electrolytes could be added so as to increase the substrate conductivity.

In some embodiments, a physical parameter that may be measured can be the dissolved oxygen in the fermentation substrate and the one or more genes that correlated with dissolved oxygen may include, but are not limited to, COX4, COX5, COX6, COX7, COX8, COX9, COX12, COX13, COX10, YAH1, ARH1, any homologue thereof, or combination thereof. If the dissolved oxygen levels of the substrate are too low, additional oxygen could be added to the fermentation vessel. If dissolved oxygen levels are too high, remediation may involve encouraging the fermenting organism to scavenge the oxygen by changing the fermentation conditions to favor oxygen scavenging, potentially by changing the fermentation temperature or mixing rate.

In some embodiments, a physical parameter that may be measured can be the temperature of the fermentation substrate and the one or more genes that correlate with temperature may include, but are not limited to, HSP104, HSP42, HSP82, CTO1, any homologue thereof, or combination thereof. If temperature is not within an acceptable parameter, the operator should adjust using their heat-exchange system if available.

In some embodiments, a physical parameter that may be measured can be cell concentration of the fermentation organism in the fermentation substrate and the one or more genes that correlate with cell concentration may include, but are not limited to CLN1, CLN2, CLN3, CLB1, CLB2, CLB3, CLB4, CLB5, CLB6, MBP1, SWI4, FKH1, FKH2, NDD1, ACE2, SWI5, HCM1, YHP1, YOX1 any homologue thereof, or combination thereof. If the cell concentration is too low, more cells of the fermenting organism can be added to increase the cell concentration. If cell concentration is too high, additional fermentation substrate could be added to the vessel where possible.

In some embodiments, modifying or adjusting a fermentation condition may comprise adding fresh yeast, verifying the presence of a contaminating organism, supplementing the fermentation substrate with a carbohydrate source or other nutrients, delaying the termination of the fermentation process, accelerating the termination of the fermentation process, increasing the temperature of the fermentation substrate, or decreasing the temperature of the fermentation substrate. Example carbohydrates for addition include, but are not limited to, glucose, lactose, galactose, maltose, maltotriose, maltotetraose, glycogen, and/or maltodextrin. Example nutrients for addition can include but are not limited to diammonium phosphate, yeast extract, vitamins, iron, zinc salts, potassium salts, magnesium salts, calcium salts, and/or sodium salts.

In some embodiments, when a contaminating organism is identified an intervention appropriate for the specific fermentation may be undertaken, up to and including terminating the fermentation). Thus, in some embodiments, when a contaminating organism is identified, the fermentation may be stopped and the fermentation system (tank and other instruments) is decontaminated/sterilized.

In the above-description of various embodiments, it is to be understood that the terminology used herein is for the purpose of describing particular embodiments only and is not intended to be limiting of the various embodiments as described herein. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

Like numbers refer to like elements throughout. Thus, the same or similar numbers may be described with reference to other drawings even if they are neither mentioned nor described in the corresponding drawing. Also, elements that are not denoted by reference numbers may be described with reference to other drawings.

When an element is referred to as being "connected," "coupled," "responsive," or variants thereof to another element, it can be directly connected, coupled, or responsive to the other element or intervening elements may be present. In contrast, when an element is referred to as being "directly connected," "directly coupled," "directly responsive," or variants thereof to another element, there are no intervening elements present. Like numbers refer to like elements throughout. Furthermore, "coupled," "connected," "responsive," or variants thereof as used herein may include wirelessly coupled, connected, or responsive. As used herein, the singular forms "a," "an," and "the" are intended to include the plural forms as well, unless the context clearly indicates otherwise. Well-known functions or constructions may not be described in detail for brevity and/or clarity. The term "and/or" includes any and all combinations of one or more of the associated listed items.

As used herein, the terms "comprise," "comprising," "comprises," "include," "including," "includes," "have," "has," "having," or variants thereof are open-ended, and include one or more stated features, integers, elements, steps, components or functions but does not preclude the presence or addition of one or more other features, integers, elements, steps, components, functions or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-Ray).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks. Accordingly, embodiments of the present disclosure may be embodied in hardware and/or in software (including firmware, resident software, microcode, etc.) that runs on a processor such as a digital signal processor, which may collectively be referred to as "circuitry," "a module," or variants thereof.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

EXAMPLES

Figure 11:
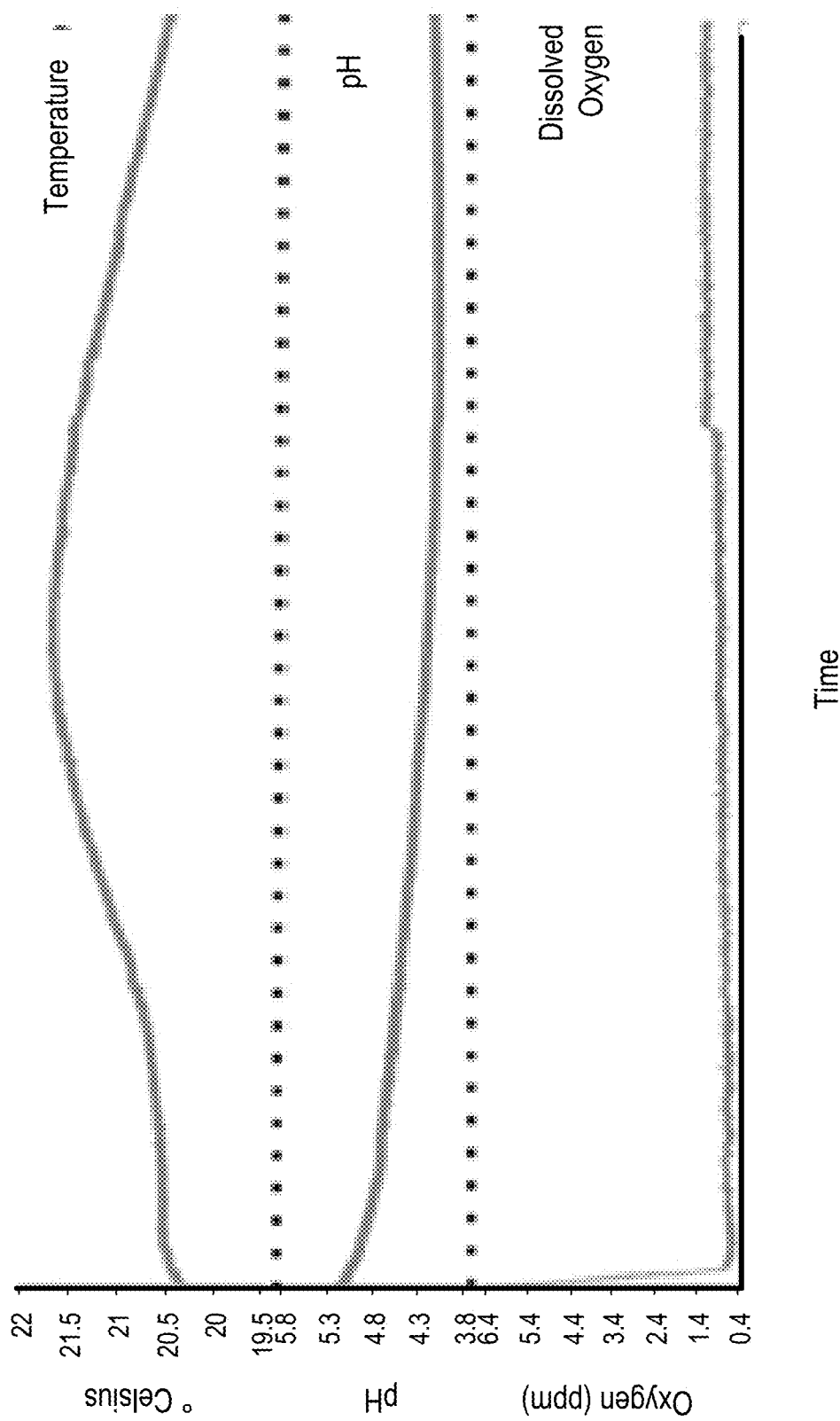
FIG. 11 illustrates an experimental implementation of a fermentation monitoring system for a yeast fermentation. Multiple parameters as measured by real-time sensors of a fermentation performance during production of beer are shown. In this example, separate sensors in the same apparatus are measuring the temperature, pH and dissolve oxygen concentration during the first 40 hours of fermentation.
Figure 12:
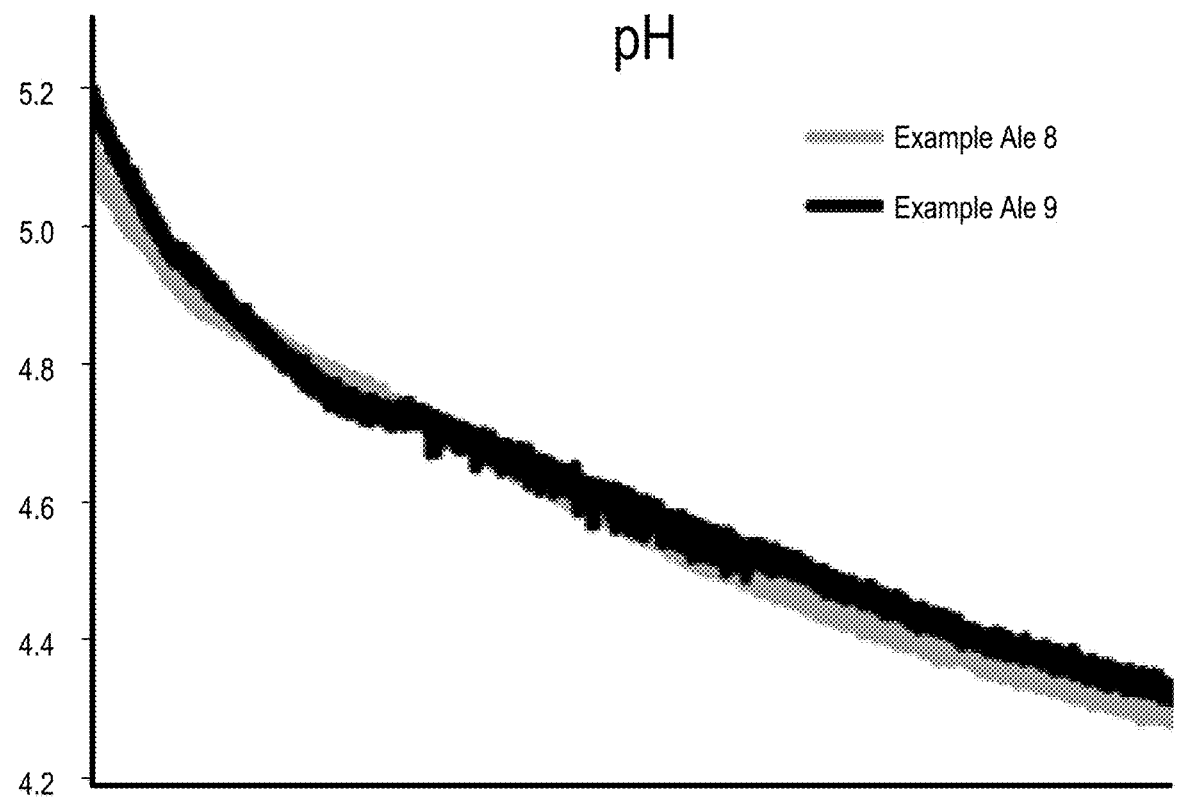
FIG. 12 illustrates another experimental implementation of a fermentation monitoring system in a yeast fermentation. pH levels as monitored using real-time sensors from two different fermentations using the same recipe brewed on different days are shown. The data is shown from initiation of fermentation through 16 hours post-initiation.

The system has been reduced to practice and fermentation performance during beer production has been monitored. The data was uploaded in real time to a database where it was accessed. These data demonstrate some of the dynamic changes in the chemical and physical properties of beer or other liquid fermentation substrates during the course of a single fermentation. See, FIGS. 11 and 12 that illustrate data from experimental implementations of a fermentation monitoring system, according to various embodiments as described herein. The data from each sensor run may be visualized separately or aligned with other data types by time (FIG. 11). Additionally, sensor data from more than one fermentation may be aligned and then visualized for the purposes of monitoring reproducibility or understanding how a change in conditions or recipe might impact fermentation performance (FIG. 12). In FIG. 11, multiple parameters as measured by real-time sensors of a fermentation performance during production of beer are shown. In this example, separate sensors in the same apparatus are measuring the temperature, pH and dissolve oxygen concentration during the first 40 hours of fermentation. In FIG. 12, pH levels as monitored using real-time sensors from two different fermentations using the same recipe brewed on different days are shown. The data provided in FIG. 12 is from initiation of fermentation through 16 hours post-initiation.

Figure 13:
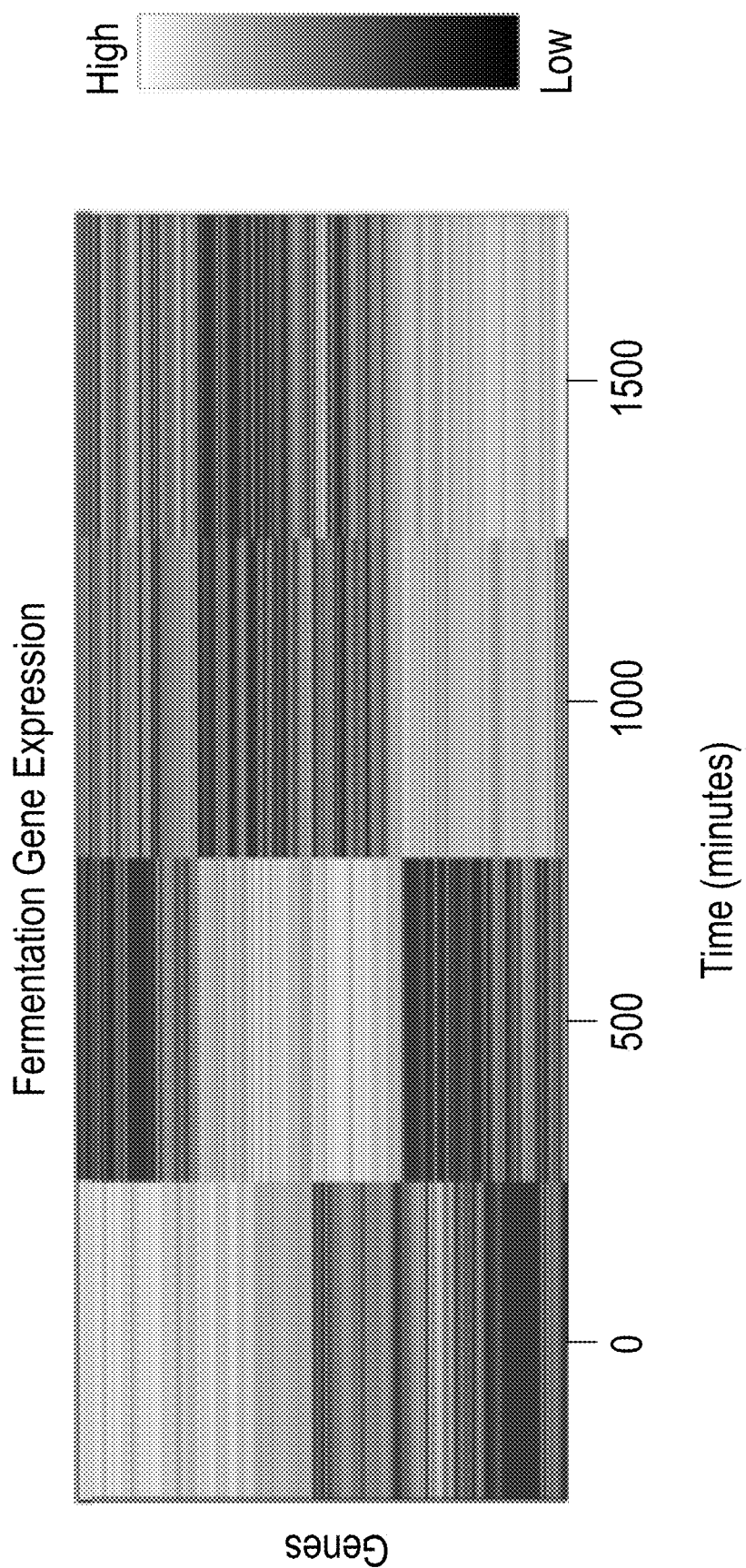
FIG. 13 is a heat map visualization of gene expression in *S. cerevisiae* during a beer fermentation from a transcriptomics analysis according to various embodiments as described herein.

FIG. 13 is a heat map visualization of gene expression in *S. cerevisiae* during a beer fermentation from a transcriptomics analysis according to various embodiments as described herein. The ~700 genes were selected during analysis for their highly dynamic behavior during beer fermentation. Each line in the graph is a single gene, and the genes are plotted from beginning to end of the fermentation analysis, left to right. In the figure, each gene is normalized to its own mean expression. When a gene is highly expressed, the block is brighter white. When the expression of the gene is low, the block appears darker. This demonstrates the dynamic behavior of gene expression during beer fermentation by budding yeast. This is a visual representation of the type of data fed into the analytical pipeline of the various embodiments as described herein.

Figure 14:
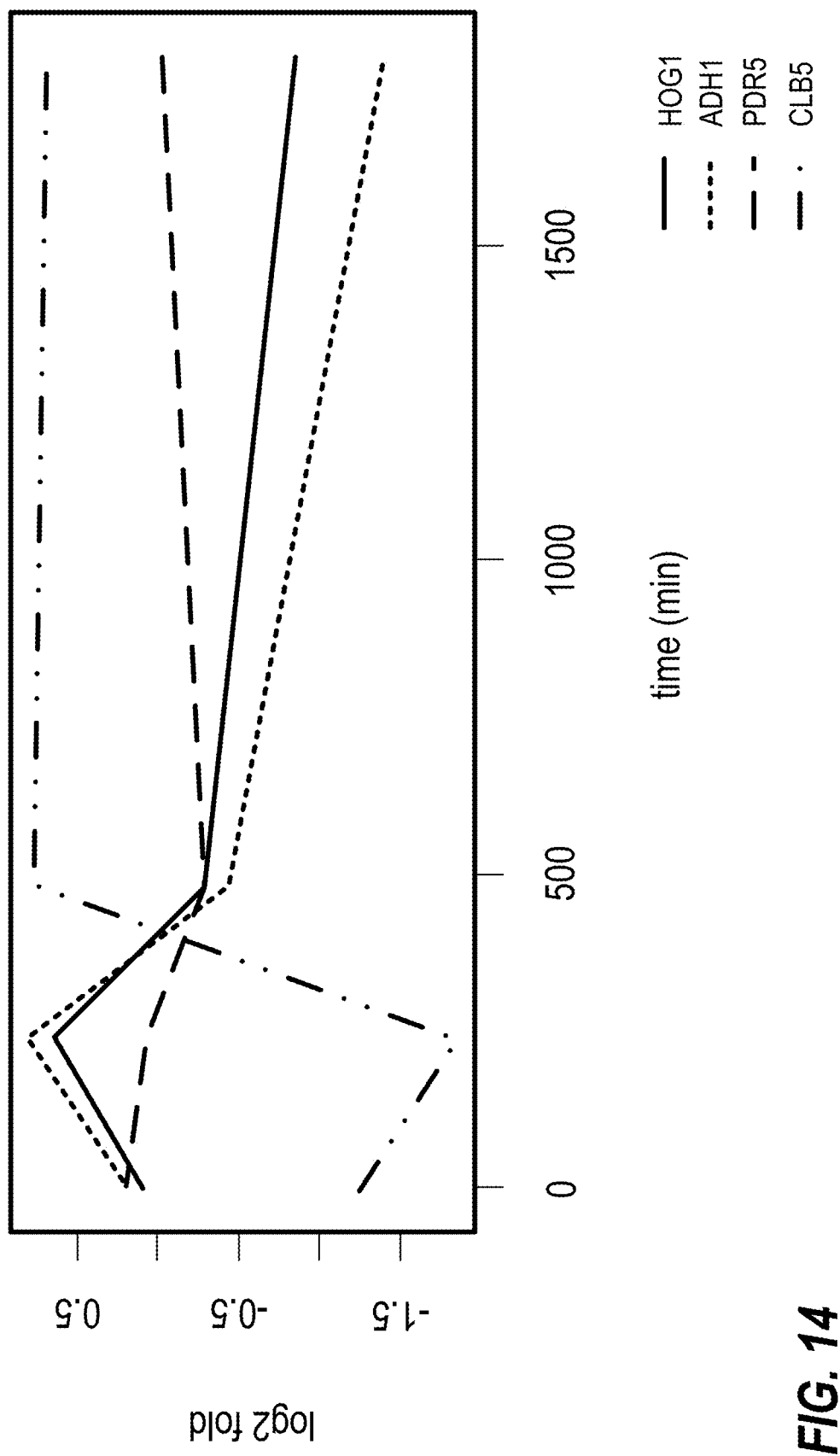
FIG. 14 is a selection of line plots of gene expression in *S. cerevisiae* during a beer fermentation from a transcriptomics analysis according to various embodiments as described herein.

FIG. 14 is a selection of line plots of gene expression in *S. cerevisiae* during a beer fermentation from a transcriptomics analysis according to various embodiments as described herein. The four genes were selected during analysis for their dynamic behavior and involvement in fermentation relevant processes. Each line is a single gene normalized to its own mean expression. These genes are plotted over time during a beer fermentation. These genes are under regulation during beer fermentation by budding yeast. This is a visual representation of the type of data fed into the analytical pipeline of the various embodiments as described herein.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of various example combinations and subcombinations of embodiments and of the manner and process of making and using them, and shall support claims to any such combination or subcombination. Many variations and modifications can be made to the embodiments without substantially departing from the principles of the present invention. All such variations and modifications are intended to be included herein within the scope of the present invention.

What is claimed is:

1. A method providing a technical solution to the technical problem of
    standardizing a selected fermentation process by a fermentation organism in a fermentation substrate, the method comprising:
    (I) first, constructing a baseline database for the selected fermentation process by the fermentation organism in the fermentation substrate by
        (a) initiating a first instance of the selected fermentation process by the fermentation organism in the fermentation substrate and obtaining, at each respective time point of a plurality of predefined time points defined from the beginning of the initiated first instance of the fermentation process, a respective fluidic sample,
        (b) measuring, using each respective fluidic sample for the first instance, one or more physical parameters for the respective fluidic sample at the corresponding respective time point,
        (c) determining one or more physical parameter values for the first instance based on the measuring for the first instance, the one or more physical parameter values including values at a point in time and values representing a rate of change,
        (d) measuring, using each respective fluidic sample for the first instance, a transcriptome of the fermentation organism at the corresponding respective time point, such measuring comprising
            (i) isolating RNA from the fermentation substrate of the respective fluidic sample,
            (ii) purifying the RNA isolated from the fermentation substrate of the respective fluidic sample, and
            (iii) measuring the RNA;
        (e) determining gene expression data for the selected fermentation process based on the obtained measurements by
            (i) filtering determined physical parameter and gene expression data to generate a first dataset which only includes dynamic physical parameter values and dynamic gene expression values,
            (ii) computationally normalizing dynamic physical parameter values and dynamic gene expression values of the first dataset to generate a normalized dataset,
            (iii) determining one or more possible regulators by identifying dynamic gene expression values of the normalized dataset that correspond to transcription factors, and
            (iv) comparing normalized dynamic physical parameter values and normalized dynamic gene expression values of the normalized dataset as targets to each determined possible regulator by
                (A) generating a regulation function for each possible regulator-target relationship, each regulation function defining a relationship between one of the determined possible regulators and a downstream gene target corresponding to one of the normalized dynamic gene expression values or a chemical change target corresponding to one of the normalized dynamic physical parameter values,
                (B) calculating, for each regulator-target relationship, a score representing a fit of the corresponding possible regulator to the corresponding target,
                (C) ranking each regulation-target relationship based on the calculated scores, and assigning a confidence value to each regulator-target relationship,
                (D) determining a confidence threshold based at least in part on data density, and
                (E) constructing a regulatory network based on the ranked regulator-target relationships and the confidence threshold,
        (f) constructing, based on the ranked regulator-target relationships and the constructed regulatory network, the baseline database for the selected fermentation process that specifies
            (i) one or more condition sets each comprising a preferred value or range of values, at one or more respective time points of the plurality of predefined time points, for one or more physical parameters that have been determined based on the ranked regulator-target relationships and the constructed regulatory network to correspond to one or more regulatory genes of the fermentation organism,
            (ii) for each physical parameter forming part of a condition set, for each of the one or more respective time points of the plurality of predefined time points, an indication of one or more regulatory genes determined based on the ranked regulator-target relationships and the constructed regulatory network to have a relationship to that physical parameter,
  (iii) for each regulatory gene indicated to have a relationship with at least one physical parameter forming part of a condition set, for each of the one or more respective time points of the plurality of predefined time points, an indication of one or more remediation actions to increase or decrease the expression of that regulatory gene;
(II) initiating, in a fermentation vessel, a standardized instance of the selected fermentation process by the fermentation organism in the fermentation substrate by
  (a) initiating a second instance of the selected fermentation process by the fermentation organism in the fermentation substrate,
  (b) automatically, at each respective time point of the plurality of predefined time points defined from the beginning of the initiated first instance of the fermentation process,
    (i) obtaining a respective fluidic sample,
    (ii) measuring, using the respective fluidic sample for the second instance, one or more physical parameters for the respective fluidic sample at the corresponding respective time point,
    (iii) determining one or more physical parameter values for the second instance based on the measuring for the second instance, the one or more physical parameter values including values at a point in time and values representing a rate of change,
    (iv) comparing determined physical parameter values for the second instance to preferred values and ranges of values specified in condition sets of the baseline database,
  (c) automatically identifying, as a result of comparing at a certain one of the time points determined physical parameter values for the second instance to preferred values and ranges of values specified in condition sets of the baseline database, a first physical parameter value for a first physical parameter which falls outside of a preferred range of values specified for the first physical parameter by a first condition set of the baseline database,
  (d) automatically determining, via lookup in the baseline database, a first regulatory gene determined based on the ranked regulator-target relationships and the constructed regulatory network to have a relationship to the first physical parameter,
  (e) automatically determining, via lookup in the baseline database, a first remediation action which will affect the expression of the determined first regulatory gene, the first remediation action comprising modifying a specified first fermentation condition,
  (f) effecting modification of the specified first fermentation condition to affect the expression of the determined first regulatory gene,
wherein the first physical parameter is density of the fermentation substrate and the first regulatory gene is ADH1 or any homologue thereof.

2. The method of claim 1, wherein the first remediation action comprises modifying the temperature in the fermentation vessel.

3. The method of claim 1, wherein the remediation action comprises an addition of a carbohydrate source to the fermentation tank.

4. The method of claim 1, wherein the baseline database includes data regarding one or more of the following possible regulatory genes: OAF1, PDR3, HIR1, HAP3, RTG3, REB1, NRG2, TEC1, SMP1, HPC2, THI2, MAL33, KAR4, HCM1, RDS1, RPN4, MBP1, PHO2, UGA3, LYS14, NRG1, PDC2, GIS1, INO2, SWI5, UME6, UPC2, ADR1, MET32, YAP6, MTH1, SUM1, ARO80, CAD1, YHP1, STP1, GCN4, MIG3, GLN3, ACA1, DOT6, FLO8, SWI4, SPT2, RPH1, GAT1, HAC1, CDC14, PHO4, PDR1, MIG1, AFT1, HSF1, TOS8, SUT1, CUP2, GTS1, IME4, MIG2, HAP2, RTG2, FZF1, RME1, MGA1, MAL13, YAP5, OPI1, RIM101, STP2, RSC30, STE12, NDT80, STB5, RPN10, SKN7, CST6, XBP1, FKH1, IMP2, GAT4, MET28, YAP5, DAL81, MGA2, ZAP1, SIP4, GZF3, CBF1, IME1, RSF2, HMS2, BYE1, PUT3, SPT23, IXR1, RGT1, PHD1, MSN4, HAP4, ABF1, ASH1, DAL80, BAS1, GAT3, PPR1, CHA4, ACE2, RFX1, SWI6, IFH1, ECM22, HAP1, PDR8, STP3, SFP1, LEU3, YAP1, YOX1, GAL80, WAR1, ARG81, SOK2, MAC1, MSN2, ARG80, MCM1, MOT3, MSS11, HOT1, RGM1, CAT8, ELP6, CRZ1, FKH2, MET4, SKO1, GCR2, SPS18, RAP1, GIS1, DAL82, YAP7, RTG1, HAL9, INO4, MSN1, CIN5, HMS1, HIR2, AZF1, SFL1, YRR1, YRM1, TYE7, HAP5, PIP2, NDD1, RDR1, MET31, GCR1, RLM1, RDS2, UME1, CUP9, AFT2, GAL4, MDL2, HAA1, YPR015C, ROX1, RDS3, FHL1, ARR1, or any homologue thereof.

5. A method providing a technical solution to the technical problem of standardizing a selected fermentation process by a fermentation organism in a fermentation substrate, the method comprising:
(I) first, constructing a baseline database for the selected fermentation process by the fermentation organism in the fermentation substrate by
  (a) initiating a first instance of the selected fermentation process by the fermentation organism in the fermentation substrate and obtaining, at each respective time point of a plurality of predefined time points defined from the beginning of the initiated first instance of the fermentation process, a respective fluidic sample,
  (b) measuring, using each respective fluidic sample for the first instance, one or more physical parameters for the respective fluidic sample at the corresponding respective time point,
  (c) determining one or more physical parameter values for the first instance based on the measuring for the first instance, the one or more physical parameter values including values at a point in time and values representing a rate of change,
  (d) measuring, using each respective fluidic sample for the first instance, a transcriptome of the fermentation organism at the corresponding respective time point, such measuring comprising
    (i) isolating RNA from the fermentation substrate of the respective fluidic sample,
    (ii) purifying the RNA isolated from the fermentation substrate of the respective fluidic sample, and
    (iii) measuring the RNA;
  (e) determining gene expression data for the selected fermentation process based on the obtained measurements by
    (i) filtering determined physical parameter and gene expression data to generate a first dataset which only includes dynamic physical parameter values and dynamic gene expression values, (ii) computationally normalizing dynamic physical parameter values and dynamic gene expression values of the first dataset to generate a normalized dataset, (iii) determining one or more possible regulators by identifying dynamic gene expression values of the normalized dataset that correspond to transcription factors, and (iv) comparing normalized dynamic physical parameter values and normalized dynamic gene expression values of the normalized dataset as targets to each determined possible regulator by (A) generating a regulation function for each possible regulator-target relationship, each regulation function defining a relationship between one of the determined possible regulators and a downstream gene target corresponding to one of the normalized dynamic gene expression values or a chemical change target corresponding to one of the normalized dynamic physical parameter values, (B) calculating, for each regulator-target relationship, a score representing a fit of the corresponding possible regulator to the corresponding target, (C) ranking each regulation-target relationship based on the calculated scores, and assigning a confidence value to each regulator-target relationship, (D) determining a confidence threshold based at least in part on data density, and (E) constructing a regulatory network based on the ranked regulator-target relationships and the confidence threshold, (f) constructing, based on the ranked regulator-target relationships and the constructed regulatory network, the baseline database for the selected fermentation process that specifies (i) one or more condition sets each comprising a preferred value or range of values, at one or more respective time points of the plurality of predefined time points, for one or more physical parameters that have been determined based on the ranked regulator-target relationships and the constructed regulatory network to correspond to one or more regulatory genes of the fermentation organism, (ii) for each condition set, one or more remediation actions determined, based on the ranked regulator-target relationships and the constructed regulatory network, to increase or decrease the expression of one or more regulatory genes of the fermentation organism determined based on the ranked regulator-target relationships and the constructed regulatory network to correspond to the respective physical parameter;

(II) initiating, in a fermentation vessel, a standardized instance of the selected fermentation process by the fermentation organism in the fermentation substrate by (a) initiating a second instance of the selected fermentation process by the fermentation organism in the fermentation substrate, (b) automatically, at each respective time point of the plurality of predefined time points defined from the beginning of the initiated first instance of the fermentation process, (i) obtaining a respective fluidic sample, (ii) measuring, using the respective fluidic sample for the second instance, one or more physical parameters for the respective fluidic sample at the corresponding respective time point, (iii) determining one or more physical parameter values for the second instance based on the measuring for the second instance, the one or more physical parameter values including values at a point in time and values representing a rate of change, (iv) comparing determined physical parameter values for the second instance to preferred values and ranges of values specified in condition sets of the baseline database, (c) automatically identifying, as a result of comparing at a certain one of the time points determined physical parameter values for the second instance to preferred values and ranges of values specified in condition sets of the baseline database, a first physical parameter value for a first physical parameter which falls outside of a preferred range of values specified for the first physical parameter by a first condition set of the baseline database, (d) automatically determining, via lookup in the baseline database, a first remediation action determined, based on the ranked regulator-target relationships and the constructed regulatory network, to increase or decrease the expression of one or more regulatory genes of the fermentation organism determined based on the ranked regulator-target relationships and the constructed regulatory network to correspond to the first physical parameter, the first remediation action comprising modifying a specified first fermentation condition, (e) effecting modification of the specified first fermentation condition to affect the expression of the determined first regulatory gene, wherein the one or more physical parameters comprises density of the fermentation substrate and the first regulatory gene is ADH1 or any homologue thereof.

6. A method providing a technical solution to the technical problem of standardizing a selected fermentation process by a fermentation organism in a fermentation substrate, the method comprising:

(I) first, constructing a baseline database for the selected fermentation process by the fermentation organism in the fermentation substrate by (a) initiating a first instance of the selected fermentation process by the fermentation organism in the fermentation substrate and obtaining, at each respective time point of a plurality of predefined time points defined from the beginning of the initiated first instance of the fermentation process, a respective fluidic sample, (b) measuring, using each respective fluidic sample for the first instance, one or more physical parameters for the respective fluidic sample at the corresponding respective time point, (c) determining one or more physical parameter values for the first instance based on the measuring for the first instance, the one or more physical parameter values including values at a point in time and values representing a rate of change, (d) measuring, using each respective fluidic sample for the first instance, a transcriptome of the fermentation organism at the corresponding respective time point, such measuring comprising (i) isolating RNA from the fermentation substrate of the respective fluidic sample,
(ii) purifying the RNA isolated from the fermentation substrate of the respective fluidic sample, and
(iii) measuring the RNA;
(e) determining gene expression data for the selected fermentation process based on the obtained measurements by
(i) filtering determined physical parameter and gene expression data to generate a first dataset which only includes dynamic physical parameter values and dynamic gene expression values,
(ii) computationally normalizing dynamic physical parameter values and dynamic gene expression values of the first dataset to generate a normalized dataset,
(iii) determining one or more possible regulators by identifying dynamic gene expression values of the normalized dataset that correspond to transcription factors, and
(iv) comparing normalized dynamic physical parameter values and normalized dynamic gene expression values of the normalized dataset as targets to each determined possible regulator by
(A) generating a regulation function for each possible regulator-target relationship, each regulation function defining a relationship between one of the determined possible regulators and a downstream gene target corresponding to one of the normalized dynamic gene expression values or a chemical change target corresponding to one of the normalized dynamic physical parameter values,
(B) calculating, for each regulator-target relationship, a score representing a fit of the corresponding possible regulator to the corresponding target,
(C) ranking each regulation-target relationship based on the calculated scores, and assigning a confidence value to each regulator-target relationship,
(D) determining a confidence threshold based at least in part on data density, and
(E) constructing a regulatory network based on the ranked regulator-target relationships and the confidence threshold,
(f) constructing, based on the ranked regulator-target relationships and the constructed regulatory network, the baseline database for the selected fermentation process that specifies
(i) one or more condition sets each comprising a preferred value or range of values, at one or more respective time points of the plurality of predefined time points, for one or more physical parameters that have been determined based on the ranked regulator-target relationships and the constructed regulatory network to correspond to one or more regulatory genes of the fermentation organism,
(ii) for each physical parameter forming part of a condition set, for each of the one or more respective time points of the plurality of predefined time points, an indication of one or more regulatory genes determined based on the ranked regulator-target relationships and the constructed regulatory network to have a relationship to that physical parameter,
(iii) for each regulatory gene indicated to have a relationship with at least one physical parameter forming part of a condition set, for each of the one or more respective time points of the plurality of predefined time points, an indication of one or more remediation actions to increase or decrease the expression of that regulatory gene;
(II) initiating, in a fermentation vessel, a standardized instance of the selected fermentation process by the fermentation organism in the fermentation substrate by
(a) initiating a second instance of the selected fermentation process by the fermentation organism in the fermentation substrate,
(b) automatically, at each respective time point of the plurality of predefined time points defined from the beginning of the initiated first instance of the fermentation process,
(i) obtaining a respective fluidic sample,
(ii) measuring, using the respective fluidic sample for the second instance, one or more physical parameters for the respective fluidic sample at the corresponding respective time point,
(iii) determining one or more physical parameter values for the second instance based on the measuring for the second instance, the one or more physical parameter values including values at a point in time and values representing a rate of change,
(iv) comparing determined physical parameter values for the second instance to preferred values and ranges of values specified in condition sets of the baseline database,
(c) automatically identifying, as a result of comparing at a certain one of the time points determined physical parameter values for the second instance to preferred values and ranges of values specified in condition sets of the baseline database, a first physical parameter value for a first physical parameter which falls outside of a preferred range of values specified for the first physical parameter by a first condition set of the baseline database,
(d) automatically determining, via lookup in the baseline database, a first regulatory gene determined based on the ranked regulator-target relationships and the constructed regulatory network to have a relationship to the first physical parameter,
(e) automatically determining, via lookup in the baseline database, a first remediation action which will affect the expression of the determined first regulatory gene, the first remediation action comprising modifying a specified first fermentation condition,
(f) displaying, to a user via an electronic display associated with the fermentation vessel,
(i) an indication of the first physical parameter,
(ii) an indication of the first physical parameter value for the first physical parameter,
(iii) an indication of the preferred range of values for the first physical parameter from the first condition set,
(iv) an indication of the first regulatory gene determined based on the ranked regulator-target relationships and the constructed regulatory network to have a relationship to that physical parameter,
(v) an indication of the first remediation action which will affect the expression of the determined first regulatory gene, the indication including an indication to modify the specified first fermentation condition, (g) effecting modification, by the user, of the specified first fermentation condition to affect the expression of the determined first regulatory gene, wherein the first physical parameter is density of the fermentation substrate and the first regulatory gene is ADH1 or any homologue thereof.

* * * * *